(12) United States Patent
Brandolini et al.

(10) Patent No.: US 12,133,843 B2
(45) Date of Patent: Nov. 5, 2024

(54) IL-8 INHIBITORS FOR USE IN THE TREATMENT AND/OR PREVENTION OF BACTERIAL SECONDARY INFECTIONS

(71) Applicant: DOMPÉ FARMACEUTICI S.P.A., Milan (IT)

(72) Inventors: Laura Brandolini, L'Aquila (IT); Marcello Allegretti, Rome (IT); Mauro Martins Teixeira, Belo Horizonte (BR)

(73) Assignee: DOMPÉ FARMACEUTICI S.P.A., Milan (IT)

( * ) Notice: Subject to any disclaimer, the term of this patent is extended or adjusted under 35 U.S.C. 154(b) by 198 days.

(21) Appl. No.: 16/616,108

(22) PCT Filed: May 28, 2018

(86) PCT No.: PCT/EP2018/063929
§ 371 (c)(1),
(2) Date: Nov. 22, 2019

(87) PCT Pub. No.: WO2018/219865
PCT Pub. Date: Dec. 6, 2018

(65) Prior Publication Data
US 2020/0101046 A1    Apr. 2, 2020

(30) Foreign Application Priority Data
May 30, 2017   (EP) ..................... 17173515

(51) Int. Cl.
*A61K 31/427*   (2006.01)
*A61P 31/04*   (2006.01)

(52) U.S. Cl.
CPC ............ *A61K 31/427* (2013.01); *A61P 31/04* (2018.01)

(58) Field of Classification Search
CPC ............................. A61K 31/427; A61P 31/04
See application file for complete search history.

(56) References Cited

U.S. PATENT DOCUMENTS

| | | | |
|---|---|---|---|
| 5,677,426 A | 10/1997 | Fong | |
| 2004/0022762 A1 | 2/2004 | Dillon | |
| 2004/0038854 A1 | 2/2004 | Dillon et al. | |
| 2016/0168233 A1* | 6/2016 | Torres ................... | A61K 39/40 424/139.1 |

FOREIGN PATENT DOCUMENTS

| | | |
|---|---|---|
| AU | 2013283022 | 5/2013 |
| EP | 2166006 | 3/2010 |
| JP | 9509837 | 10/1997 |
| JP | 2004509147 | 3/2004 |
| WO | WO 1995/023865 | 9/1995 |
| WO | WO 2000/024710 | 5/2000 |
| WO | WO2004058797 | 7/2004 |
| WO | WO 2005/090295 | 9/2005 |
| WO | WO2010031835 | 3/2010 |
| WO | WO2014205127 | 12/2014 |
| WO | WO2017009323 | 1/2017 |

OTHER PUBLICATIONS

Robinson et al., The Journal of Infectious Diseases, vol. 209, Issue 6, Mar. 15, 2014, pp. 865-875.*
Kemp DM, et al., "Ladarixin, & dual CKC21/2 inhibitor, attenuates experimental melanomas harboring different molecular defects by affecting malignant cells and tumor microenvironment", Oncotarget, 2017, vol. 8 (No. 9), pp. 14428-14442.
Lopes, et al., "DF275SA, a novel non-competitive allosteric inhibitor of CXCR3./2, reduces inflammatory and post-operative pain", Pharmacological Research, 383 (2016), pp. 69-79.
Liderdt, K. , et al. , "Secondary Bacterial Infections in Patients with Seasonal Influenza A and Pandemic H1N1", Biomed Res Int., vol. 2033, Article 376219, 2013, pp. 1-6.
Morris, D.E., et al., "Secondary Bacterial Infections Associated with Influenza Pandemics", Front. Microbiol. 2017, vol. 5, Article 1041, pp. 1-17.
Tavares, Luciane, P., et al., "CXCR1/2 antagonism is Protective during Influenza and Post- influenza Pneumococcal Infection", Front Immunol, Dec. 13, 2017, vol. 8, Article 1799, pp. 1-14.
Barnes, Peter, J., "New treatments for copd", Nature Reviews, vol. 1, Jun. 2002, pp. 437-445.
Bertini, R., et al., "Receptor binding mode and pharmacological characterization of a potent and selective dual CXCR1/CXCR2 non-competitive allosteric inhibitor", British Journal of Pharmacology, 165, 2012, pp. 436-454.
Bertini, Riccardo, et al. "Noncompetitive allosteric inhibitors of the inflammatory chemokine receptors CXCR1 and CXCR2: prevention of reperfusion injury", PNAS, vol. 101, No. 32, Aug. 10, 2004, pp. 11791-11796.
Cheyne, Leanne, et al., "Tiotropium versus ipratropium bromide for chronic obstructive pulmonary disease", Cochrane Database of Systematic Reviews, Issue 9, Art. No. CD009552. 2013, pp. 1-28.
Chiu, C.T., et al., "Reparixin attenuates neuronal injury in experimental Klebsiella pneumoniae meningoencephalitis through dual effects on neuroprotection and neuroinflammation", Neuropathology and Applied Neurobiology, 42, 2016, pp. 326-343.
Cunha, TM, et al., "Treatment with DF 2162, a non-competitive allosteric inhibitor of CXCR1/2, diminishes neutrophil influx and inflammatory hypernociception in mice", British Journal of Pharmacology, 154, 2008, pp. 460-470.
Dominguez-Cherit, Guillermo, et al., "Critically ill ptients with 2009 influenza A(H1N1) in Mexico", JAMA, vol. 302, No. 17, Nov. 4, 2009, pp. 1880-1887.
Fincham, N J, et al., "Neutrophil chemoattractant and IL-1-like activity in sample from psoriatic skin lesion. Further characterization", The Journal of Immunology, 140, 1988. pp. 4294-4299.
Garcia, Cristiana Couto, et al., "The development of anti-inflammatory drugs for infectious diseases", Discovery Medicine, vol. 10, No. 55, Dec. 2010, pp. 479-488.
Garnock-Jones, Karly, P., "Roflumilast: A review in COPD", Drugs, 75, 2015, pp. 1645-1656.

(Continued)

*Primary Examiner* — Alicia L Otton
(74) *Attorney, Agent, or Firm* — HUESCHEN AND SAGE

(57) ABSTRACT

The present invention relates to IL-8 inhibitor compounds, preferably dual CXCR1/CXCR2 receptor inhibitors, useful in the treatment and/or prevention of secondary bacterial infections, preferably secondary respiratory infections.

6 Claims, 11 Drawing Sheets

(56) References Cited

OTHER PUBLICATIONS

Griffin, Thomas, D., et al., "Clinical and histologic heterogeneity of psoriatic plaques", Arch Dermatol, vol. 124, Feb. 1988, pp. 216-220.
Gupta, Ravindra, K., et al., "Bacterial pneumonia and pandemic influenza planning", Emerging Infectious Diseases, vol. 14, No. 8, Aug. 2008, pp. 1187-1192.
Hidaka, hideki, et al., "Curcumin inhibits interleukin 8 production and enhances interleukin 8 receptor expression on the cell surface", Cancer, 95, 2002, pp. 1206-1214.
International Search Report for PCT/EP2018/063929 dated Sep. 4, 2018.
Jain. Seema, et al.. "Hospitalized patients with 2009 H1N1 influenza in the United States, Apr.-Jun. 2009", The New England Journal of Medicine, 365:20, Nov. 12, 2009, pp. 1935-1944.
Jeffery, Peter, K., "Comparison of the structural and inflammatory features of COPD and asthma", Chest, 117:5, May 2000 Supplement, pp. 251S-260S.
Jeffery, Peter, K., "Structural and inflammatory changes in COPD: a comparison with asthma", Thorax, 53, 1998, pp. 129-136.
José, Ricardo, et al., "Regulation of neutrophilic inflammation in lung injury induced by community-acquired pneumonia", Poster Abstracts, Feb. 26, 2015, pp. 52.
Karlström, Åsa, et al., "Toll-like receptor 2 mediates fatal immunopathology in mice during treatment of secondary pneumococcal pneumonia following influenza", The Journal of Infectious Diseases, 204, 2011, pp. 1358-1366.
Klein, Eili, Y., et al., "The frequency of influenza and bacterial coinfection: a systematic review and meta-analysis", Influenza and Other Respiratory Viruses, 10(5), 2016, pp. 394-403.
Kolaczkowska, Elzbieta, et al., "Neutrophil recruitment and function in health and inflammation", Immunology, vol. 13, Mar. 2013, pp. 159-175.
Kopf, Manfred, et al., "The development and function of lung-resident macrophages and dendritic cells", Nature Immunology, vol. 16, No. 1, Jan. 2015, pp. 1-9.
Lefer, Allan, M., et al. "Cardioprotective and endothelial protective effects [Ala-IL8]77 in a rabbit model of myocardial ischemia and reperfusion", Br. J. Pharmacol, 103, 1991, pp. 1153-1159.
Liu, Zhi, et al., "A major role for neutrophils in experimental bullous pemphigoid", The Journal of Clinical Investigation, vol. 100., No. 5, Sep. 1997, pp. 1256-1263.
Mackay, Alex, J., et al., "COPD exacerbatons causes, prevention, and treatment", Med Clin N Am, 96, 2012, pp. 789-809.
Madhi, Shabir, A., et al., "A role for *Streptococcus pneumoniae* in virus-associated pneumonia", Nature Medicine, vol. 10, No. 8., Aug. 2004, pp. 811-813.
McCullers, Jonathan, A., "Insights into the interaction between influenza virus and pneumococcus", Clinical Microbiology Review, Jul. 2006, pp. 571-582.
Oostwoud, L.C., et al., "Apocynin and ebselen reduce influenza A virus-induced lung inflammation in cigarette smoke-exposed mice", Scientific Reports, 6:20983, Feb. 15, 2016, pp. 1-16.
Palacios, Gustavo, et al., "*Streptococcus pneumoniae* coinfection is correlated with the severity of H1N1 pandemic influenza", PLOS One, vol. 4, Issue 12, e8540, Dec. 2009, pp. 1-5.

Pesci, A., et al., "Inflammatory cells and mediators in bronchial lavage of patients with chronic obstructive pulmonary disease", Eur Respir J, 12, 1998, pp. 380-386.
Rabe, Klaus, F., et al., "Global strategy for the diagnosis, management, and prevention of chronic obstructive pulmonary disease", Am J Respir Crit Care Med, vol. 176, 2007, pp. 532-555.
Ramos, Irene, et al., "Modulating the innate immune response to influenza A virus: potential therapeutic use of anti-inflammatory drugs", Front. Immunol., 6:361, Jul. 2015, pp. 1-19.
Romson, Joseph, L., et al., "Reduction of the extent of ischemic myocardial injury by neutrophil depletion in the dog", Circulation, 67, 1983, pp. 1016-1023.
Russo, Remo, C., et al., "Role of the chemokine receptor CXCR2 in bleomycin-induced pulmonary inflammation and fibrosis", 2009, pp. 1-44.
Russo, Remo, C., et al., "The CXCL8/IL-8 chemokine family and its receptors in inflammatory diseases", Expert Rev. Clin. Immunol., 10(5), 2014, pp. 593-619.
Sekido, Nobuaki, et al., "Prevention of lung reperfusion injury in rabbits by a monoclonal antibody against interleukin-8", Nature, vol. 365, Oct. 14, 1993, pp. 654-657.
Short, Kirsty, R., et al., "Interactions between *Streptococcus pneumoniae* and influenza virus: a mutually beneficial relationship", Future Microbiol., 7(5), 2012, pp. 609-624.
Takematsu, Hideaki, et al., "Quantification of chemotactic peptides (C5a anaphylatoxin and IL-8) in psoriatic lesional skin", Arch Dermatol, vol. 129, Jan. 1993, pp. 74-80.
Tavares, Luciana, P., et al., "Inhibition of phosphodiesterase-4 during pneumococcal pneumonia reduces inflammation and lung injury in mice", American Journal of Respiratory Cell and Molecular Biology, vol. 55, No. 1, Jul. 2016, pp. 24-34.
Teow, Sin-Yeang, et al., "Antibacterial action of curcumin against *Staphylococcus aureaus*: a brief review", Journal of Tropical Medicine, vol. 2016, Article 2853045, pp. 1-10.
Wang, Jennifer, P., et al., "Toll-like receptor-mediated activation of neutrophils by influenza A virus", Blood, vol. 112, No. 5, Sep. 1, 2008, pp. 2028-2034.
Welbourn, C.R.B, et al., "Pathophysiology of ischaemia reperfusion injury: central role of the neutrophil", Br. J. Surg., vol. 78, Jun. 1991, pp. 651-655.
Wolf, Walter, et al., "Tumor-based pharmacokinetics has greater significance for anticancer drugs than does blood-based pharmacokinetics", Clinical Pharmacology & THERAPEUTICS, Nov. 2004, pp. 508.
Liderot, et al., BioMed Research International, vol. 2013, Article ID 376219, 6 pages.
Metzger, et al., J. Immunol., 2013, 191, 2047-2052.
Morris, et al., Front. Microbiol., Jun. 23, 2017, vol. 8, Article 1041.
Leitner, et al., International Journal of Immunology and Pharmacology, 2007, 20, 25-36.
Shahangian, et al., J. Clin. Invest., 2009, 119, 1910-1920.
Garcia, et al., "The therapeutic potential of targeting the chemokine receptor CXCR2 in murine models of lung primary and secondary infections", Options IX for the Control of Influenza, International Society for Influenza and Other Respiratory Virus Diseases. Aug. 25, 2016.
Slupsky, et al., Journal of Proteome Research, 2009, 8, 3029-3036.
Garcia, Cristiana, "Targeting the Chemokine Receptor CXCR2 in Murine Models of Primary and Secondary Lung Infections: Therapeutic Potential?", 8th Annual Gabriel Network Meeting. 2016.

\* cited by examiner

IL-8 INHIBITORS FOR USE IN THE TREATMENT AND/OR PREVENTION OF BACTERIAL SECONDARY INFECTIONS

TECHNICAL FIELD

The present invention relates to IL-8 inhibitors for the prevention and/or treatment of secondary bacterial infections, preferably secondary respiratory infections. Said secondary bacterial infections are associated with a preceding influenza infection, sepsis, severe ischemia or reperfusion injury.

BACKGROUND ART

The lungs are composed of a myriad of tree-like ramifications that end in intensively vascularized alveoli. The mucosal surface of the lung is incredibly large (90 $m^2$) and is exposed daily to a high number of particles and microorganisms including pathogens [Kopf, M., C. Schneider, and S. P. Nobs, *The development and function of lung-resident macrophages and dendritic cells*. Nat Immunol, 2015. 16(1): p. 36-44]. Therefore a great number of physical and biological barriers, including the innate immune system, protect the lungs from a possible infection. Pro-inflammatory cytokines and chemokines are produced by resident immune cells and lung epithelial cells promoting the recruitment of neutrophils and the onset of inflammation, important to control the dissemination and proliferation of microorganisms. However, the uncontrolled inflammatory response triggered by infection may also lead to increased lung damage, morbidity and mortality [Garcia, C. C., et al., *The development of anti-inflammatory drugs for infectious diseases*. Discov Med, 2010. 10(55): p. 479-88].

Influenza A virus (IAV) is a respiratory pathogen of great worldwide relevance, causing 3 to 5 million of severe illness and more than 300.000 deaths during epidemics. Secondary bacterial infections contribute greatly to the increased mortality and morbidity during seasonal flu and also pandemics. It is estimated that bacterial co-infections are responsible for approximately 25% of influenza related deaths [Gupta, R. K., R. George, and J. S. Nguyen-Van-Tam, *Bacterial pneumonia and pandemic influenza planning*. Emerg Infect Dis, 2008. 14(8): p. 1187-92]. Among different bacteria related to secondary flu infections, *Streptococcus pneumoniae* (*S. pneumoniae*) is one of the most common causative pathogens [Short, K. R., et al., *Interactions between Streptococcus pneumoniae and influenza virus: a mutually beneficial relationship?* Future Microbiol, 2012. 7(5): p. 609-24] and is considered as a primary cause of mortality during seasonal flu [McCullers, J. A., *Insights into the interaction between influenza virus and pneumococcus*. Clin Microbiol Rev, 2006. 19(3): p. 571-82]. Indeed, *S. pneumoniae* is a leading cause of community-acquired pneumonia among children and adults, especially those who presented flu previously [Madhi, S. A., K. P. Klugman, and G. Vaccine Trialist, *A role for Streptococcus pneumoniae in virus-associated pneumonia*. Nat Med, 2004. 10(8): p. 811-3]. Despite the availability of antibiotics, the incidence and lethality of pneumococcal secondary infections after flu is still high. In fact, during IAV and pneumococcus coinfection, treatment with antibiotics causes bacteria lysis, excessive stimulation of the immune system and massive recruitment of neutrophils, events that may lead to intense tissue damage and mortality [Karlstrom, A., et al., *Toll-like receptor 2 mediates fatal immunopathology in mice during treatment of secondary pneumococcal pneumonia following influenza*. J Infect Dis, 2011. 204(9): p. 1358-66].

Neutrophils are the main inflammatory cells recruited into the lungs during IAV and pneumococcal infections [Jose, R., et al., *Regulation of neutrophilic inflammation in lung injury induced by community-acquired pneumonia*. Lancet, 2015. 385 Suppl 1: p. S52]. Once the microorganisms reach the lung epithelium they are recognized by immune and non-immune cells leading to secretion of chemokines such as CXCL8 (CXCL1/CXCL2 in mice) [Wang, J. P., et al., *Toll-like receptor-mediated activation of neutrophils by influenza A virus*. Blood, 2008. 112(5): p. 2028-34]. These chemokines act through its receptors CXCR1 and CXCR2 expressed in a myriad of cell types such as monocytes, CD8+ T cells, natural killers and neutrophils. In neutrophils, activation of CXCR1 and CXCR2 leads to chemotaxis, release of granule enzymes and production of reactive oxygen species [Russo, R. C., et al., *The CXCL8/IL-8 chemokine family and its receptors in inflammatory diseases*. Expert Rev Clin Immunol, 2014. 10(5): p. 593-619]. These events are very important to control virus or bacteria proliferation and dissemination, but overwhelming activation of neutrophils can be detrimental for the host as it can lead to intense lung injury. This is true for both IAV and pneumococcus infections, as an intense influx of highly activated neutrophils are associated with disease severity [Ramos, I. and A. Fernandez-Sesma, *Modulating the Innate Immune Response to Influenza A Virus: Potential Therapeutic Use of Anti-Inflammatory Drugs*. Front Immunol, 2015. 6: p. 361; Tavares, L. P., et al., *Inhibition of PDE4 During Pneumococcal Pneumonia Reduces Inflammation and Lung Injury in Mice*. Am J Respir Cell Mol Biol, 2015]. Therefore, strategies to control the inflammatory response during respiratory infections could reduce disease magnitude.

As mentioned above, a preceding influenza infection may increase the risk of a subsequent bacterial (other pathogens) infection. This situation is not unique to influenza as other types of severe infections (e.g. sepsis) may cause a similar situation in experimental systems and contribute to the enhanced lethality rates observed after sepsis in humans. Other severe conditions may also associate with the risk of a secondary infection, including severe ischemia and reperfusion injury. Interleukin-8 (IL-8; CXCL8) is considered a major mediator of PMN (Polymorphonuclear Neutrophils) recruitment and is involved in several pathologies including psoriasis, rheumatoid arthritis, chronic obstructive pulmonary disease and reperfusion injury in transplanted organ (Griffin et al, Arch Dermatol 1988, 124: 216; Fincham et al, J Immunol 1988, 140: 4294; Takematsu et al, Arch Dermatol 1993, 129: 74; Liu et al, 1997, 100:1256; Jeffery, Thorax 1998, 53: 129; Pesci et al, Eur Respir J. 1998, 12: 380; Lafer et al, Br J Pharmacol. 1991, 103: 1153; Romson et al, Circulation 1993, 67: 1016; Welbourn et al, Br J Surg. 1991, 78: 651; Sekido et al, Nature 1993, 365, 654). The biological activity of IL-8 is mediated by the interaction with two receptors, CXCR1 and CXCR2, belonging to the 7TM-GPCR family, that are expressed on the surface of human PMNs. While CXCR1 is selective, binding with high affinity only two chemokines, CXCL6 and IL-8, and showing a much higher affinity for IL-8 (Wolf et al, Eur J Immunol 1998, 28: 164), human CXCR2 is a more promiscuous receptor, binding a number of different cytokines and chemokines. Therefore, CXCR2 mediates the activity of a number of different biological molecules.

SUMMARY OF THE INVENTION

In connection with bacterial infections and as reported above, the present inventors observed that in neutrophils, activation of CXCR1 and CXCR2 leads to chemotaxis, release of granule enzymes and production of reactive oxygen species which are very important to control bacteria proliferation and dissemination. In view of the above, there was no motivation to use the IL-8 inhibitors for the treatment of bacterial infections. As matter of fact, infections that are caused by bacteria are treated with antibiotics.

The present inventors have surprisingly found that the modulation of the inflammatory response by blocking CXCR1/CXCR2 improves disease outcome, without compromising immune response against the pathogens during secondary infections, preferably respiratory infections, and more preferably pneumococcal infections.

Accordingly, a first object of the present invention is an IL-8 inhibitor selected from small molecular weight molecules, preferably a CXCR1 inhibitor, more preferably a dual CXCR1/CXCR2 inhibitor, for use in the prevention and/or treatment of secondary bacterial infections, preferably secondary respiratory infections, more preferably pneumococcal infections.

The second object of the present invention is the use of said IL-8 inhibitor as defined above, for the preparation of a medicament for the prevention and/or treatment of secondary bacterial infections, preferably secondary respiratory infections, more preferably pneumococcal infections.

The third object of the present invention is a method for the prevention and/or treatment of secondary bacterial infections, preferably secondary respiratory infections, more preferably pneumococcal infections, comprising the step of administering to a subject in need thereof a therapeutically effective amount of said IL-8 inhibitor, as defined above.

The fourth object of the invention is a pharmaceutical composition for the prevention and/or treatment of secondary bacterial infections, preferably secondary respiratory infections, more preferably pneumococcal infections, comprising an IL-8 inhibitor according to the invention and pharmaceutically acceptable excipients and/or diluents.

According to one preferred embodiment, said secondary respiratory infections are associated with a preceding influenza infection, sepsis, severe ischemia or reperfusion injury.

After 14 days of IAV infection, mice were secondary infected with *S. pneumoniae* ($10^3$ CFU, i.n.). Single infections were also performed. Mock mice were instilled (i.n.) with PBS. The lethality (A) and weight loss (B) were accompanied. In another experiment, mice under the same treatments and infection conditions were euthanized after 48 h after the second infection. Number of total leukocytes (C) and neutrophils (D) in the airways, neutrophils in the lungs (E-MPO assay) and bacteria in BALF (F) or in blood (G) were accessed. The results are presented as Mean±SEM. * for $P<0,05$;  for $P<0,01$ and * for $P<0.001$ when compared to Mock group; ## for $P<0,01$ and ### for $P<0.001$ when compared to Vehicle group (n=10 mice per group).

Figure 6:
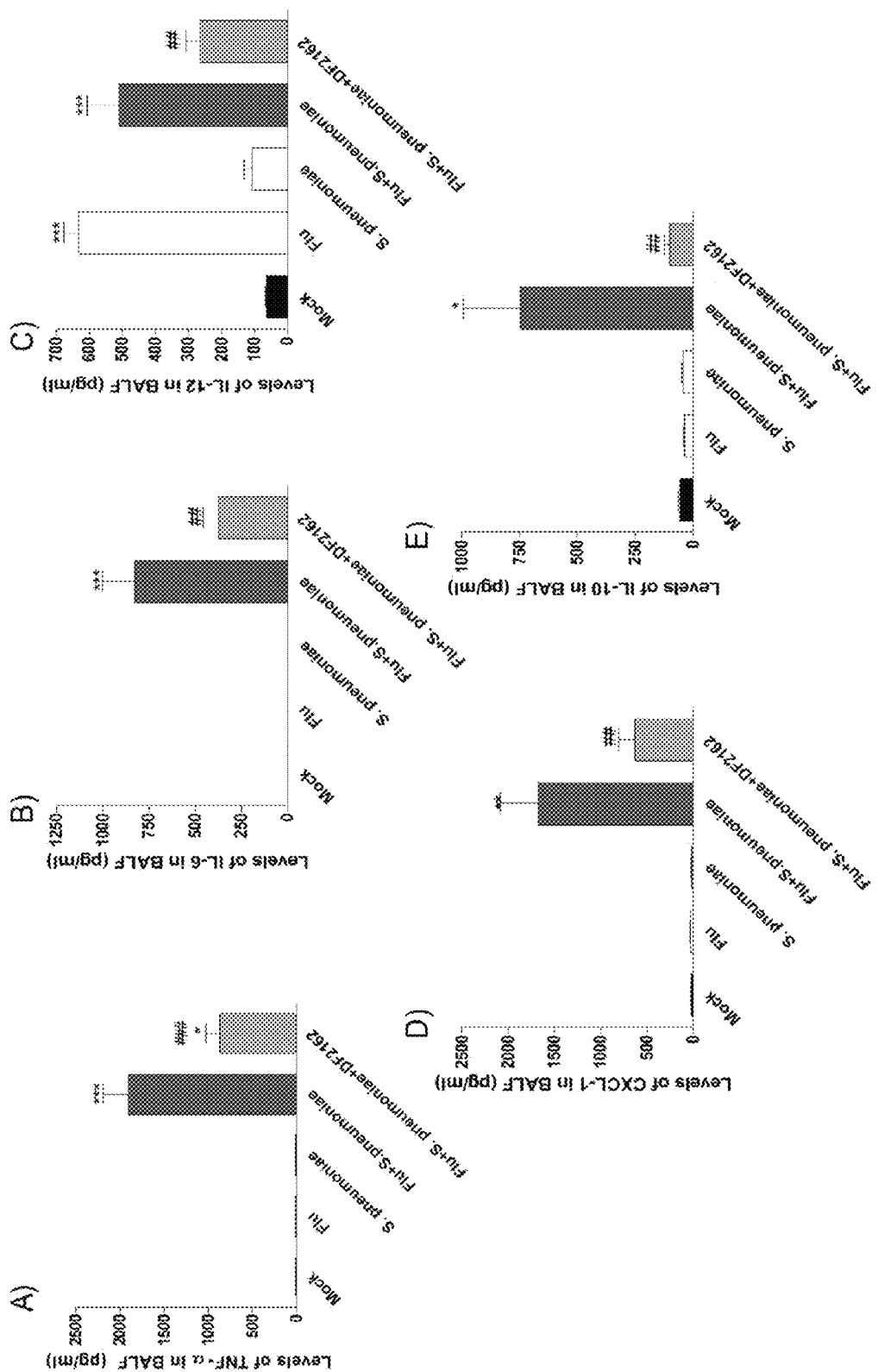

FIG. 6. CXCR1/CXCR2 antagonism during IAV primary infection reduced the levels of cytokines during pneumococcal secondary infection. Mice were infected with IAV ($5×10^2$ PFU, i.n.) and at 3, 4, 5, and 6 days after infection were treated twice a day with DF2162 (10 mg/kg—oral gavage) or the vehicle of the drug. The animals only received the drug during the IAV infection. After 14 days of IAV infection, mice were secondary infected with *S. pneumoniae* ($10^3$ CFU, i.n.). Single infections were also performed. Mock mice were instilled (i.n.) with PBS. After 48 hours of the *S. pneumoniae* infection mice were euthanized and the levels of TNF-α (A), IL-6 (B), IL-12 (C), CXCL-1 (D) and IL-10 (E) were measured in the BAL fluid. Data are presented as Mean±SEM. * for P<0,05;  for P<0,01 and * for P<0.001, when compared to Mock group; ## for P<0,01 and ### for P<0.001 when compared to Vehicle group (n=10 mice per group).

Figure 7:
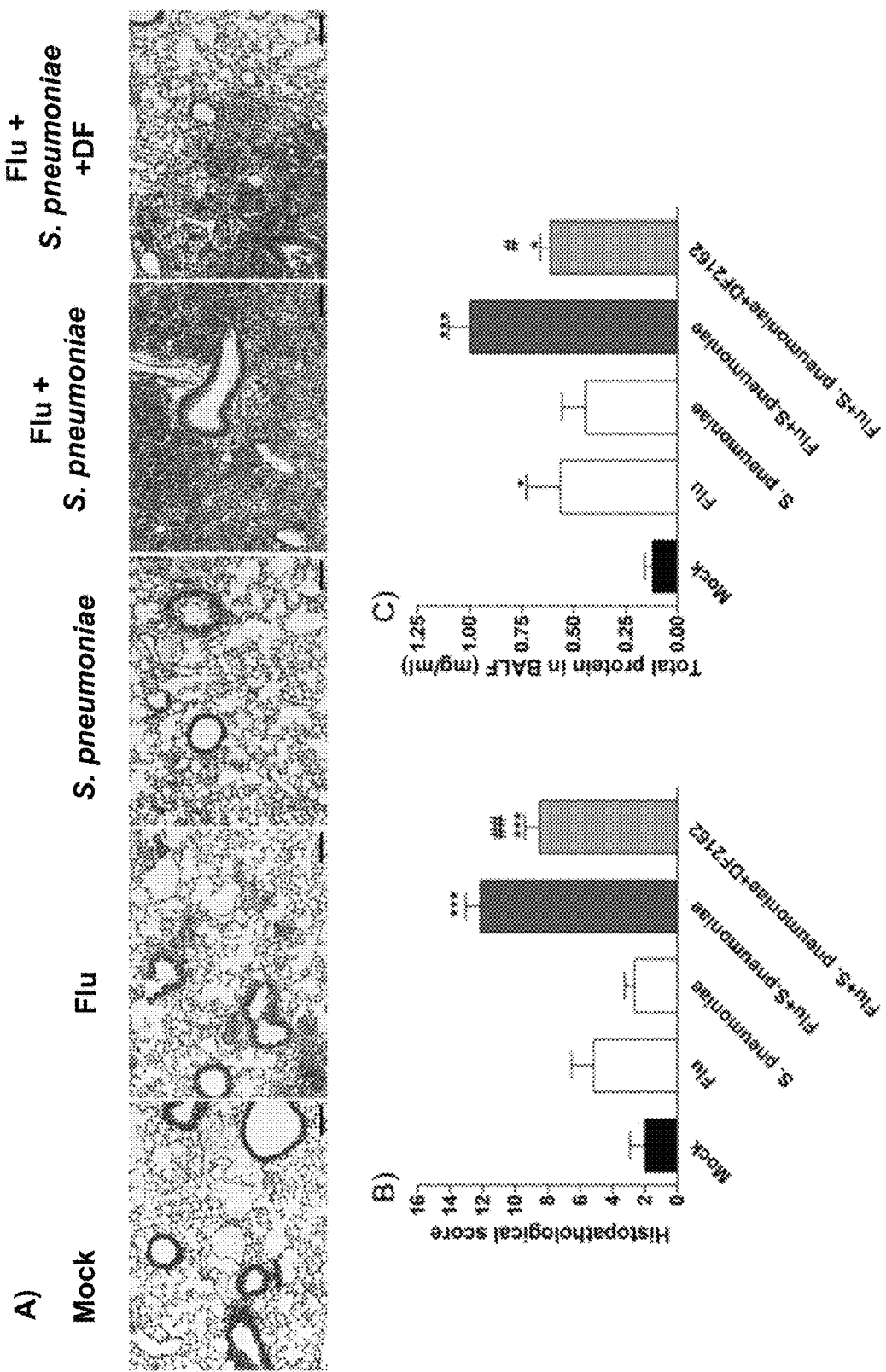

FIG. 7. Increased lung injury due to secondary pneumococcal infection is reduced after DF2162 treatment. Mice were infected with IAV ($5 \times 10^2$ PFU, i.n.) and at 3, 4, 5, and 6 days after infection were treated twice a day with DF2162 (10 mg/kg—oral gavage) or the vehicle of the drug. The animals only received the drug during the IAV infection. After 14 days of IAV infection, mice were secondary infected with S. pneumoniae ($10^3$ CFU, i.n.). Single infections were also performed. Mock mice were instilled (i.n.) with PBS. After 48 h of secondary infection, lungs were collected, processed and histological analysis were performed. Representative slides of Mock, single infected mice (IAV and S. pneumoniae) and secondary infected mice (vehicle and DF2162-treated) are shown in A (bars represent 150 μm in magnification of 100×). Graph B shows the overall score of lung injury of infected mice. BAL fluid was used to measure the protein leakage due to infection (C). Data are presented as Mean±SEM. * for P<0,05;  for P<0,01 and * for P<0.001, when compared to Mock group; # for P<0,05 and ## for P<0.01 when compared to Vehicle group (n=10 mice per group).

Figure 8:
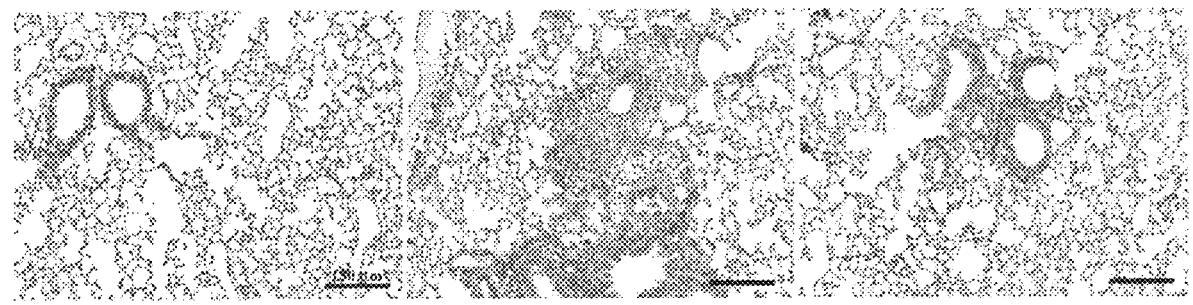

FIG. 8. Histopathological changes in the lungs of IAV infected mice are reduced after DF2162 treatment. Mice were infected with $10^4$ PFU of IAV and treated with DF2162 (10 mg/kg) twice a day during the first 5 days of infection or with the drug vehicle (CMC 0.1% in PBS). Control animals were instilled intranasally with PBS (Mock). Representative H&E stained slides of lungs of Mock and IAV-infected animals (vehicle and DF-treated) are shown—100× magnifications.

Figure 9:
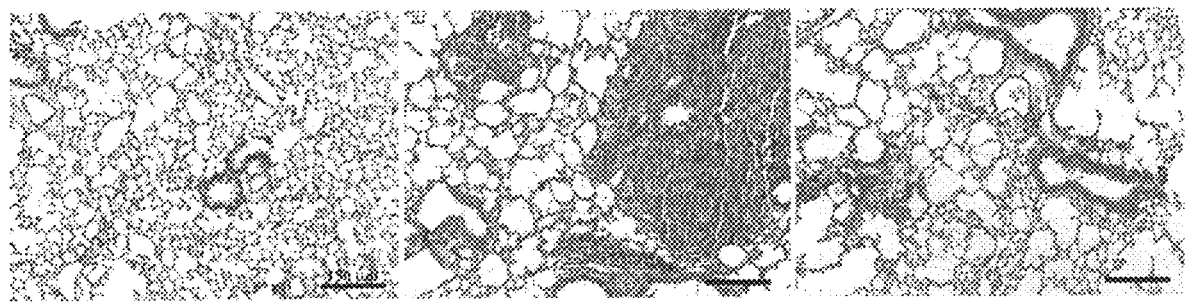

FIG. 9. Treatment with CXCR1/CXCR2 antagonist prevents histopathological changes in the lungs of S. pneumoniae infected mice. Mice were infected intranasally with $10^4$ CFU of S. pneumoniae or PBS (Mock) and treated with DF2162 (10 mg/kg) twice a day during the first 2 days of infection or with the drug vehicle (CMC 0.1% in PBS). Representative H&E stained slides of lungs of Mock and S. pneumoniae-infected animals (vehicle and DF-treated) are shown—100× magnifications.

Figure 10:
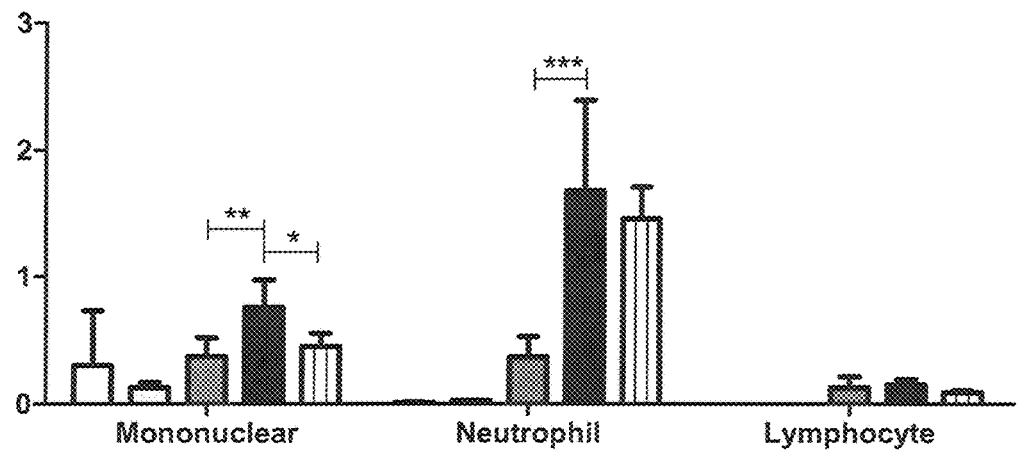
Figure 10:
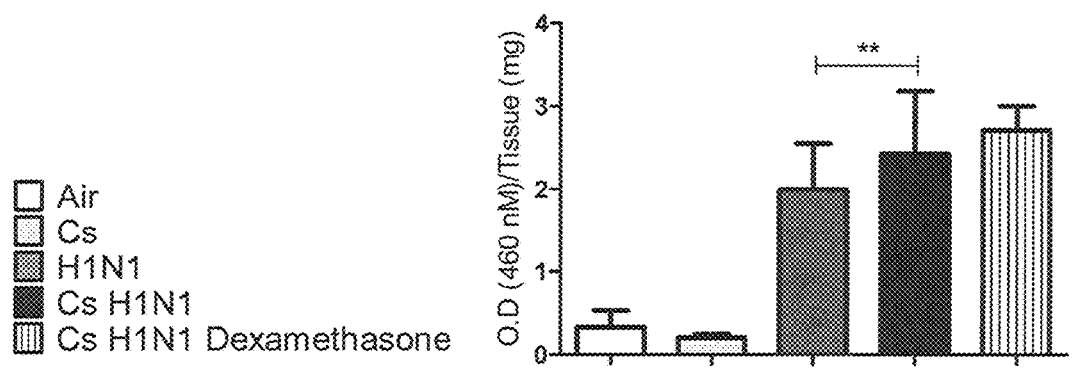
Figure 10:
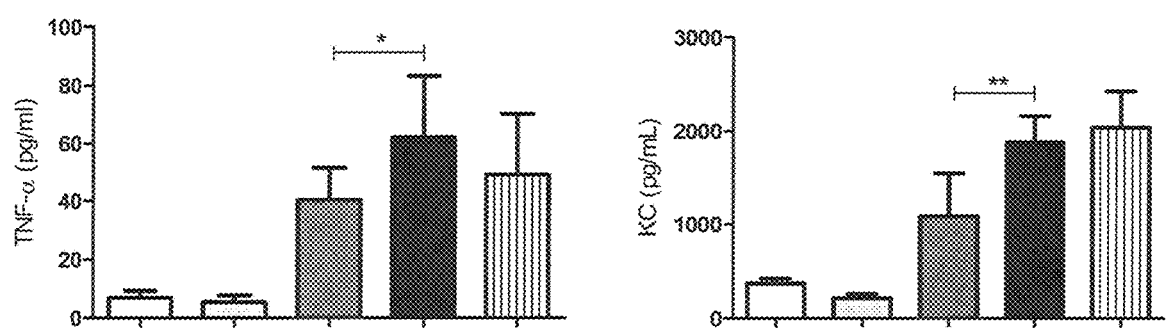

FIG. 10. Dexamethasone treatment in Cs-H1N1 mice. (A) Citokine concentration in lung tissue, (B) Total leucocyte numbers obtained from BAL analyses and (C) MPO activity in lung tissue of mice exposed to Ambient Air (Air), Cigarette smoke (Cs), infected with H1N1 virus (H1N1), Infected with H1N1 virus and exposed to Cs (Cs H1N1) and Cs H1N1 treated with dexamethasone (1 mg/kg p.o) once a day 48 hs after infection during 4 days (Cs H1N1 Dexamethasone).

Figure 11:
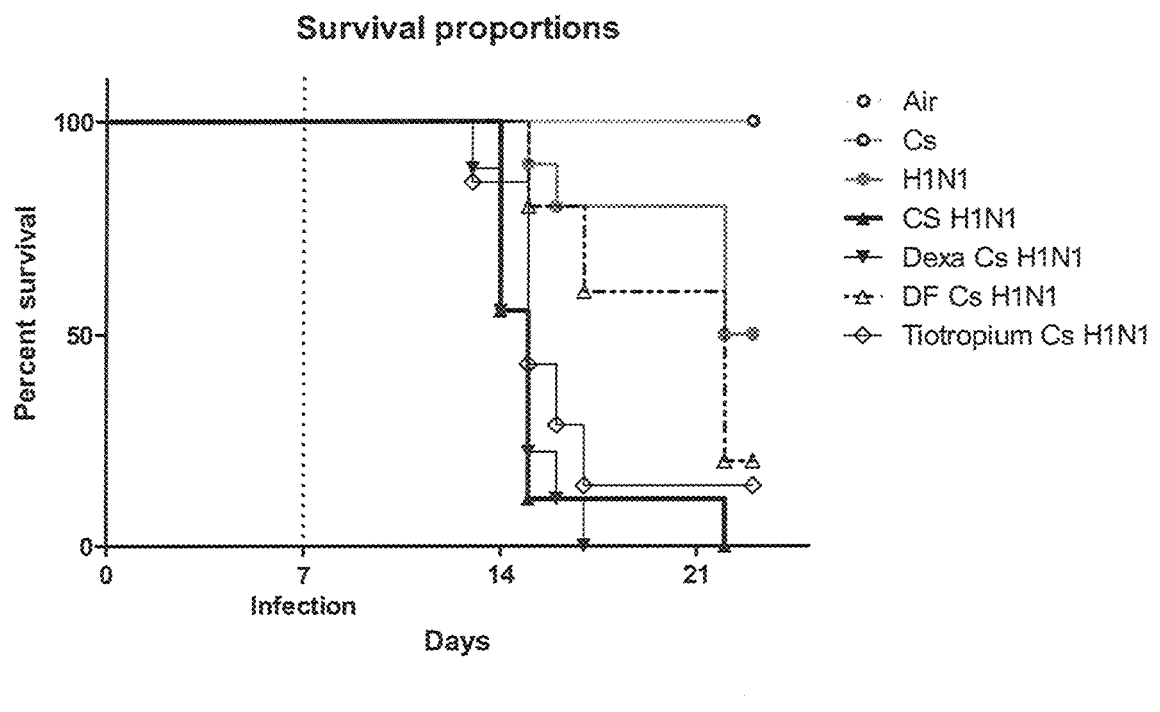

FIG. 11. Survival assay treating Cs-H1N1 mice with DF2156A, a CXCR1/CXCR2 antagonist. Survival proportions of mice exposed to Ambient Air (Air), Cigarette smoke (Cs), infected with H1N1 virus (H1N1), Infected with H1N1 virus and exposed to Cs (Cs H1N1), Cs H1N1 treated with dexamethasone (1 mg/kg) once a day during 7 days starting the day of infection (Cs H1N1 Dexamethasone v.o), Cs H1N1 treated with DF2156A (10 mg/kg p.o) once a day during 7 days starting the day of infection and Cs H1N1 treated with 3 ml of Tiotropium (0,3 mg/ml aerosol) once a day during 7 days starting the day of infection.

DETAILED DESCRIPTION OF THE INVENTION

As it will be disclosed in details in the Experimental Section, the present inventors have found that molecules of the invention acting as inhibitors of IL-8 activity, preferably dual CXCR1/CXCR2 receptor inhibitors, have therapeutic efficacy in the treatment and/or prevention of secondary bacterial infections.

Accordingly, a first object of the present invention is an IL-8 inhibitor for use in the treatment and/or prevention of secondary bacterial infections, preferably secondary respiratory infections, more preferably pneumococcal infections, wherein the IL-8 inhibitor is selected from small molecular weight molecules.

According to a preferred embodiment, said secondary bacterial infections are associated with a preceding influenza infection, sepsis, severe ischemia or reperfusion injury.

The term "IL-8-inhibitor" according to the present application refers to any compound able to inhibit, partially or totally, the biological activity of IL-8. Such a compound can act by decreasing the expression or activity of IL-8 or by inhibiting the triggering of the intracellular signaling activated by the IL-8 receptors. It is preferred that said IL-8 inhibitor is able to inhibit at least 50%, preferably at least 60%, of the chemotaxis induced by IL-8 in PMNs at a concentration equal or below 500 nM, preferably below 100 nM.

According to a preferred embodiment, the IL-8 inhibitor of all the objects of the present invention inhibits the activity of IL-8 mediated by CXCR1 receptor or mediated by both CXCR1 and CXCR2 receptors.

Preferably, according to this embodiment, said IL-8 inhibitor is either an allosteric inhibitor or an orthosteric antagonist of CXCR1 receptor or of both CXCR1 and CXCR2 receptors.

Preferably, said IL-8 inhibitor is selective for CXCR1 receptor or is equally potent towards CXCR1 and CXCR2 receptors. More preferably, said IL-8 inhibitor is equally potent towards CXCR1 and CXCR2 receptors.

By "selective for CXCR1" according to the present invention it is meant a compound that shows an $IC_{50}$ value at least 2, preferably 3, logs higher toward CXCR1 than towards CXCR2. (Bertini R. et al., Proc. Nat. Acad. Sci. USA (2004), 101 (32), pp. 11791-11796).

By "equally potent towards CXCR1 and CXCR2" it is meant a compound that shows an $IC_{50}$ value in the range 10 picomolar ($10^{-11}$M)-1 micromolar ($10^{-6}$M) towards CXCR1 and CXCR2. (Bertini R. et al., Br. J. Pharm. (2012), 165, pp. 436-454).

More preferably, the IL-8 inhibitor according to the invention has an $IC_{50}$ value towards CXCR1 receptor in the low nanomolar range, preferably in the range 0.02-5 nanomolar.

According to the present invention, also in combination with the preceding embodiment, said IL-8 inhibitor is selected from small molecular weight molecules. According to an alternative embodiment, said IL-8 inhibitor is selected from antibodies, preferably anti-CXCR1/CXCR2 receptor antibodies.

IL-8 inhibitors according to the above definition, able to inhibit the activity of IL-8 mediated by CXCR1 receptor or mediated by both CXCR1 and CXCR2 receptors, are known in the art.

Preferred IL-8 inhibitors according to the invention are dual CXCR1/CXCR2 receptor inhibitors selected from 1,3-thiazol-2-ylaminophenylpropionic acid derivatives, 2-phenyl-propionic acid derivatives and their pharmaceutically acceptable salts.

Among the above compounds, said 1,3-thiazol-2-ylaminophenylpropionic acid derivative is preferably a compound of formula (I):

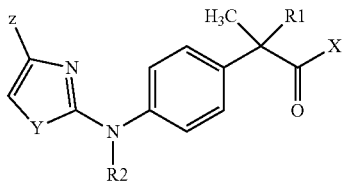

(I)

or a pharmaceutically acceptable salt thereof, wherein
R1 is hydrogen or $CH_3$;
R2 is hydrogen or linear $C_1$-$C_4$ alkyl, preferably it is hydrogen;
Y is a heteroatom selected from S, O and N; preferably it is S;
Z is selected from halogen, linear or branched $C_1$-$C_4$ alkyl, $C_2$-$C_4$ alkenyl, $C_2$-$C_4$ alkynyl, $C_1$-$C_4$ alkoxy, hydroxyl, carboxyl, $C_1$-$C_4$ acyloxy, phenoxy, cyano, nitro, amino, $C_1$-$C_4$ acylamino, halo $C_1$-$C_3$ alkyl, halo $C_1$-$C_3$ alkoxy, benzoyl, linear or branched $C_1$-$C_8$ alkanesulfonate, linear or branched $C_1$-$C_8$ alkanesulfonamide, linear or branched $C_1$-$C_8$ alkylsulfonylmethyl; preferably it is trifluoromethyl;
X is OH or a residue of formula $NHR_3$; wherein $R_3$ is selected from:
hydrogen, hydroxyl, linear or branched $C_1$-$C_6$ alkyl, $C_3$-$C_6$ cycloalkyl, $C_2$-$C_6$ alkenyl, $C_1$-$C_5$ alkoxy, or $C_1$-$C_6$ phenylalkyl, wherein alkyl, cycloalkyl or alkenyl group can be substituted by a COOH residue;
a residue of formula $SO_2R4$ wherein R4 is $C_1$-$C_2$ alkyl, $C_3$-$C_6$ cycloalkyl, $C_1$-$C_3$ haloalkyl.
Preferably, in the above compounds X is OH.
Among the above compounds, particularly preferred are compounds of said formula (I) or pharmaceutically acceptable salts thereof, wherein:
R1 is $CH_3$;
R2 is hydrogen or linear $C_1$-$C_4$ alkyl, preferably it is hydrogen;
Y is a heteroatom selected from S, O and N; preferably it is S;
Z is selected from halogen, linear or branched $C_1$-$C_4$ alkyl, $C_2$-$C_4$ alkenyl, $C_2$-$C_4$ alkynyl, $C_1$-$C_4$ alkoxy, hydroxyl, carboxyl, $C_1$-$C_4$ acyloxy, phenoxy, cyano, nitro, amino, $C_1$-$C_4$ acylamino, halo $C_1$-$C_3$ alkyl, halo $C_1$-$C_3$ alkoxy, benzoyl, linear or branched $C_1$-$C_8$ alkanesulfonate, linear or branched $C_1$-$C_8$ alkanesulfonamides, linear or branched $C_1$-$C_8$ alkylsulfonylmethyl; preferably it is trifluoromethyl;
X is OH or a residue of formula $NHR_3$; wherein $R_3$ is selected from:
hydrogen, hydroxyl, linear or branched $C_1$-$C_6$ alkyl, $C_3$-$C_6$ cycloalkyl, $C_2$-$C_6$ alkenyl, $C_1$-$C_5$ alkoxy, or $C_1$-$C_6$ phenylalkyl, wherein alkyl, cycloalkyl or alkenyl group can be substituted by a COOH residue;
a residue of formula $SO_2R4$ wherein R4 is $C_1$-$C_2$ alkyl, $C_3$-$C_6$ cycloalkyl, $C_1$-$C_3$ haloalkyl.
Preferably, in these compounds X is OH.
Among the above compounds, particularly preferred are also compounds of said formula (I) or pharmaceutically acceptable salts thereof, wherein
R1 is hydrogen;
R2 is hydrogen or linear $C_1$-$C_4$ alkyl, preferably it is hydrogen;
Y is a heteroatom selected from S, O and N; preferably it is S;
Z is selected from halogen, linear or branched $C_1$-$C_4$ alkyl, $C_2$-$C_4$ alkenyl, $C_2$-$C_4$ alkynyl, $C_1$-$C_4$ alkoxy, hydroxyl, carboxyl, $C_1$-$C_4$ acyloxy, phenoxy, cyano, nitro, amino, $C_1$-$C_4$ acylamino, halo $C_1$-$C_3$ alkyl, halo $C_1$-$C_3$ alkoxy, benzoyl, linear or branched $C_1$-$C_8$ alkanesulfonate, linear or branched $C_1$-$C_8$ alkanesulfonamides, linear or branched $C_1$-$C_8$ alkylsulfonylmethyl; preferably it is selected from trifluoromethyl;
X is OH or a residue of formula $NHR_3$; wherein $R_3$ is selected from
hydrogen, hydroxyl, linear or branched $C_1$-$C_6$ alkyl, $C_3$-$C_6$ cycloalkyl, $C_2$-$C_6$ alkenyl, $C_1$-$C_5$ alkoxy, or $C_1$-$C_6$ phenylalkyl, wherein alkyl, cycloalkyl or alkenyl group can be substituted by a COOH residue;
a residue of formula $SO_2R4$ wherein R4 is $C_1$-$C_2$ alkyl, $C_3$-$C_6$ cycloalkyl, $C_r$-$C_3$ haloalkyl.
More preferably X is $NH_2$.
Preferably, in the above compounds X is OH.
Among the above compounds, particularly preferred are also compounds of said formula (I) or pharmaceutically acceptable salts thereof, wherein:
R1 is hydrogen or $CH_3$;
R2 is hydrogen or linear $C_1$-$C_4$ alkyl, preferably it is hydrogen;
Y is a heteroatom selected from S, O and N; preferably it is S;
Z is selected from linear or branched $C_1$-$C_4$ alkyl, linear or branched $C_1$-$C_4$ alkoxy, halo $C_1$-$C_3$ alkyl and halo $C_1$-$C_3$ alkoxy; preferably it is selected from methyl, methoxy, trifluoromethoxy, trifluoromethyl, more preferably it is trifluoromethyl;
X is OH.
Among the above compounds, particularly preferred are also compounds of said formula (I) or pharmaceutically acceptable salts thereof, wherein:
R1 is $CH_3$;
R2 is hydrogen or linear $C_1$-$C_4$ alkyl, preferably it is hydrogen.
Y is a heteroatom selected from S, O and N; preferably it is S.
Z is selected from linear or branched $C_1$-$C_4$ alkyl, linear or branched $C_1$-$C_4$ alkoxy, halo $C_1$-$C_3$ alkyl and halo $C_1$-$C_3$ alkoxy; preferably it is selected from methyl, methoxy, trifluoromethoxy, trifluoromethyl, more preferably it is trifluoromethyl.
Among the above compounds, particularly preferred are also compounds of said formula (I) or pharmaceutically acceptable salts thereof, wherein
R1 is hydrogen;
X is OH;
R2 is hydrogen or linear $C_1$-$C_4$ alkyl, preferably it is hydrogen;
Y is a heteroatom selected from S, O and N; preferably it is S;
Z is selected from linear or branched $C_1$-$C_4$ alkyl, linear or branched $C_1$-$C_4$ alkoxy, halo $C_1$-$C_3$ alkyl and halo $C_1$-$C_3$ alkoxy; preferably it is trifluoromethyl.
Preferably, in all of the above compounds of formula (I) wherein R1 is hydrogen, the chiral carbon atom of the phenylpropionic group is in the S configuration. Particularly preferred are compounds of formula (I) according to the invention selected from 2-methyl-2-(4-{[4-(trifluoromethyl)-1,3-thiazol-2-yl]amino} phenyl)propanoic acid (herein indicated also as DF2726Y) and pharmaceutically acceptable salts thereof, preferably its sodium salt (herein indicated also as DF2726A) and 2-(4-{[4-(trifluoromethyl)-1,3-thiazol-2-yl]amino}phenyl)propanoic acid and pharmaceutically acceptable salts thereof, preferably (2S)-2-(4-{[4-(trifluoromethyl)-1,3-thiazol-2-yl] amino} phenyl) propanoic acid (also known as DF2755Y) and its sodium salt, also known as DF2755A.

Compounds of formula (I) are disclosed in WO2010/031835, which also discloses their method of synthesis, their activity as IL-8 inhibitors as well as their use in the treatment of IL-8 dependent pathologies such as transient cerebral ischemia, bullous pemphigoid, rheumatoid arthritis, idiopathic fibrosis, glomerulonephritis and damages caused by ischemia and reperfusion.

Among the above IL-8 inhibitors, said 2-phenyl-propionic acid derivative is preferably a compound of formula (II):

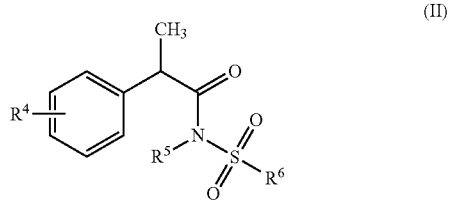

(II)

or a pharmaceutically acceptable salt thereof,
wherein
$R^4$ is linear or branched $C_1$-$C_6$ alkyl, benzoyl, phenoxy, trifluoromethanesulfonyloxy; preferably it is selected from benzoyl, isobutyl and trifluoromethanesulfonyloxy. Also, according to a preferred embodiment $R^4$ is in position 3 or 4 on the phenyl ring, more preferably it is 3-benzoyl, 4-isobutyl or 4-trifluoromethanesulfonyloxy.

$R^5$ is H or linear or branched $C_1$-$C_3$ alkyl, preferably it is H;

$R^6$ is linear or branched $C_1$-$C_6$ alkyl or trifluoromethyl, preferably, it is a linear or branched $C_1$-$C_6$ alkyl, more preferably it is $CH_3$.

Among the above compounds, preferred are compounds of formula (II) or a pharmaceutically acceptable salts thereof, wherein:
$R^4$ is $C_1$-$C_6$ alkyl or benzoyl; preferably it is in positions 3 and 4, more preferably, it is 3-benzoyl or 4-isobutyl.

$R^5$ is H or linear or branched $C_1$-$C_3$ alkyl, preferably it is H, $R^6$ is linear or branched $C_1$-$C_6$ alkyl or trifluormethyl; preferably it is a linear or branched $C_1$-$C_6$ alkyl, more preferably it is $CH_3$.

Among the above compounds, preferred are compounds of formula (II) or a pharmaceutically acceptable salts thereof, wherein:
$R^4$ is trifluoromethanesulfonyloxy, preferably 4-trifluoromethanesulfonyloxy, $R^5$ is H or linear or branched $C_1$-$C_3$ alkyl, preferably it is H, $R^6$ is linear or branched $C_1$-$C_6$ alkyl or trifluormethyl; preferably it is a linear or branched $C_1$-$C_{16}$ alkyl, more preferably it is $CH_3$.

Among the above compounds, also preferred are compounds of formula (III):

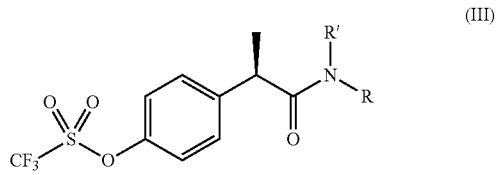

(III)

or a pharmaceutically acceptable salts thereof,
wherein
R' is hydrogen;
R is H or a residue of formula $SO_2Ra$ wherein Ra is linear or branched $C_1$-$C_4$ alkyl or halo $C_1$-$C_3$ alkyl, preferably Ra is $CH_3$.

Preferably, in the above compound of formula (II) or (III), the chiral carbon atom of the phenylpropionic group is in the R configuration.

Particularly preferred compounds of formula (II) according to the invention are selected from R-(−)-2-(4-isobutylphenyl)propionyl methansulfonamide (also known as Reparixin) and pharmaceutically acceptable salts thereof. Preferably, said compound is the lysine in situ salt of R-(−)-2-(4-isobutylphenyl)propionyl methansulfonamide (herein indicated also as DF1681B).

Further particularly preferred compounds of formula (II) or (III) according to the invention are 2-(4-trifluoromethanesulfonyloxy)phenyl]-N-methanesulfonyl propionamide and pharmaceutically salts thereof, preferably its sodium salt preferably R(−)-2-(4-trifluoromethanesulfonyloxy)phenyl]-N-methanesulfonyl propionamide (also known as DF2156Y) and its sodium salt (also known as Ladarixin or DF2156A).

Further particularly preferred compound of formula (III) according to the invention is R(−)-2-[(4'-trifluoromethanesulfonyloxy)phenyl]propionamide (also known as DF2162).

IL-8 inhibitors of formula (II) and (III) are disclosed in WO0024710 and WO2005/090295, that also disclose their method of synthesis, their activity as IL-8 inhibitors as well as their use as inhibitors of neutrophils chemotaxis and degranulation induced by IL-8 and in the treatment of IL-8 dependent pathologies such as psoriasis, ulcerative colitis, melanoma, chronic obstructive pulmonary diseases (COPD), bullous pemphigoid, rheumatoid arthritis, idiopathic fibrosis, glomerulonephritis and damages caused by ischemia and reperfusion.

The second object of the present invention is the use of an IL-8 inhibitor, as defined above, for the preparation of a medicament for the treatment and/or prevention of secondary bacterial infections, preferably secondary respiratory infections, more preferably pneumococcal infections.

According to a preferred embodiment of the present invention, said medicament is for the treatment and/or prevention of secondary bacterial infections associated with a preceding influenza infection, sepsis, severe ischemia or reperfusion injury.

The third object of the present invention is a method for the treatment and/or prevention of secondary bacterial infections, preferably secondary respiratory infections, more preferably pneumococcal infections, comprising the step of administering to the subject in need thereof, a therapeutically effective amount of an IL-8 inhibitor, as defined above.

According to a preferred embodiment of the present invention, said method is for the treatment and/or prevention of secondary bacterial infections associated with a preceding influenza infection, sepsis, severe ischemia or reperfusion injury.

As used herein, a "therapeutically effective amount" refers to an amount sufficient to achieve treatment or prevention of the disease. Determination of the effective amounts is well within the capability of those skilled in the art based upon the achievement of a desired effect. An effective amount will depend on factors including, but not limited to, the weight of a subject and/or the degree of the disease or unwanted condition from which a subject suffers.

The terms "treatment" and "prevention" as used herein refer to the eradication/amelioration or prevention/delay in onset, respectively, of the disorder being treated or of one or more of the symptoms associated thereof, notwithstanding the fact that the patient may still be afflicted with the underlying disorder.

The fourth object of the present invention is a pharmaceutical composition comprising an IL-8 inhibitor, as defined above, for use in the treatment and/or prevention of secondary bacterial infections, preferably secondary respiratory infections, more preferably pneumococcal infections, in association with pharmaceutically acceptable excipients and/or diluents.

According to a preferred embodiment, said secondary bacterial infections are associated with a preceding influenza infection, sepsis, severe ischemia or reperfusion injury.

For the purpose of the present invention, the inhibitors of IL-8 according to the present invention are formulated in pharmaceutical compositions suitable for use by oral formulation, such as tablets, capsules, syrups, preferably in the form of controlled release formulations, or by parenteral administration, preferably in the form of sterile solutions suitable for intravenous or intramuscular administration. The pharmaceutical compositions can be prepared according to conventional methods, for example as disclosed in Remington, "The Science and Practice of Pharmacy", 21st ed. (Lippincott Williams and Wilkins).

The average daily dose depends on several factors such as the severity of the disease, the condition, age, sex and weight of the patient. The dose will vary generally from 1 to 1500 mg of compounds of formula (I) per day optionally divided in multiple administrations.

The invention will be further illustrated in greater details in the following experimental section.

EXPERIMENTAL SECTION

Example 1

Materials and Methods

Mice

Male C57BL/6J mice (8-12 weeks old) were obtained from the Central Animal Facility from Universidade Federal de Minas Gerais (CEBIO UFMG/Brazil) and were maintained with free access to commercial chow and water. All procedures described had prior approval of the local animal ethics committee (CETEA/UFMG 13/2010 and 381/2015).

Bacterial and Virus Strains

*Streptococcus pneumoniae* (ATCC 6303 serotype 3) was grown for 12 hours on blood agar plates at 37° C. and 5% $CO_2$ and infection stocks were prepared as described [Tavares, L.P., et al., *Inhibition of PDE4 During Pneumococcal Pneumonia Reduces Inflammation and Lung Injury in Mice*. Am J Respir Cell Mol Biol, 2015]. The inocula were always confirmed by plating of bacterial suspension.

The mouse adapted virus Influenza A/WSN/33 H1N1—herein called IAV—was grown in MDCK (Madin-Darby Canine Kidney) cultured cells as described [Garcia, C. C., et al., *Platelet-activating factor receptor plays a role in lung injury and death caused by Influenza A in mice*. PLoS Pathog, 2010. 6(11): p. e1001171]. Prior to infection, the stocks were thawed on ice and diluted in sterile phosphate buffered saline (PBS).

Mice Infections

For IAV and *S. pneumoniae* single infections, mice were anesthetized with 60 mg/kg of ketamine and 4 mg/kg of xylazine and instilled intranasally with $10^4$ PFU of IAV or $10^4$ CFU of *Streptococcus pneumoniae*. For the secondary pneumococcal infection model, anesthetized mice were infected with 500 PFU of IAV and after 14 days of viral infection, mice were anesthetized with isofluorane and then infected with $10^3$ CFU of *S. pneumoniae*. Control mice received PBS (Mock infection).

Treatment Protocol

In order to evaluate the effect of CXCR1/CXCR2 antagonism during the respiratory infections, mice were treated with the CXCR1/CXCR2 non-competitive allosteric antagonist, R(−)-2-[(4'-trifluoromethanesulfonyloxy)phenyl]propionamide (DF2162) (100 μl-10 mg/kg) diluted in 0.1% carboxymethylcellulose (CMC) by oral gavage. Vehicle treated animals received 100 μl of 0.1% of CMC only [Russo, R. C., et al., *Role of the chemokine receptor CXCR2 in bleomycin-induced pulmonary inflammation and fibrosis*. Am J Respir Cell Mol Biol, 2009. 40(4): p. 410-21]. This dose and schedule of administration have been shown to cause significant inhibition of neutrophil influx in other models and are consistent with the long half-life of the molecule [Cunha, T. M., et al., *Treatment with DF 2162, a non-competitive allosteric inhibitor of CXCR1/2, diminishes neutrophil influx and inflammatory hypernociception in mice*. Br J Pharmacol, 2008. 154(2): p. 460-70].

For the single IAV infection, infected mice ($10^4$ PFU) were treated twice a day for 5 days from the day of infection. Mice were euthanized after 5 days of infection to access inflammation, virus titer and lung damage. Weight loss was also accompanied.

For the pneumococcal single infection, infected mice ($10^5$ CFU) were treated after 6 hours of infection and then after 12, 24 and 36 hours. After 48 hours of infection, mice were euthanized for evaluation of lung injury, bacteria counts and inflammation.

For the lethality experiments, mice were treated twice a day for 2 days and accompanied for 10 days.

Lastly, for the secondary pneumococcal infection experiments mice were infected with 500 PFU of IAV and treated from day 3 to 6 of infection (twice a day). After 14 days of IAV infection, mice were infected with $10^3$ CFU *S. pneumoniae*. Lethality and weight loss were accompanied. Mice were euthanized after 16 days of IAV infection (2 days after pneumococcus infection) for analysis of lung damage, inflammation and bacteria counts in the airways and blood.

Bronchoalveolar Lavage (BAL) and Tissue Extraction

At indicated time points, mice were euthanized with a lethal dose of ketamine/xylazine (180 mg/kg and 15 mg/kg, respectively), blood was collected for bacteria counts and bronchoalveolar lavage (BAL) was performed. For that, mice trachea was exposed, a 1.7 mm catheter was inserted and two aliquots of 1 ml of PBS were flushed three times into the brochoalveolar compartment to recover the leukocytes and bacteria in the airways of mice [Garcia, C. C., et al., *Platelet-activating factor receptor plays a role in lung injury and death caused by Influenza A in mice*. PLoS Pathog, 2010. 6(11): p. e1001171]. 100 µl of BAL fluid were plated in blood agar for bacterial counts. After centrifugation, the pellet of cells was used to total and differential cell counts. BAL fluid supernatants were used for cytokines (IL-12p40, IL-10, TNF-α, IL-6, CXCL1 and CXCL2) measurements by ELISA according to manufacturer instructions (R&D Systems, USA) and total protein quantification using the Bradford assay (Biorad). The right lung of mice was collected for indirect quantification of neutrophil recruitment into the tissue (myeloperoxidase assay—MPO) and for virus titration. The left lobe of the lungs was fixed in formalin for further histological examination.

Lung Myeolperoxidase Assay

Fifty mg of lung tissue were homogenized in a buffered solution containing antiproteases, as previously described [Russo, R. C., et al., *Role of the chemokine receptor CXCR2 in bleomycin-induced pulmonary inflammation and fibrosis*. Am J Respir Cell Mol Biol, 2009. 40(4): p. 410-21]. MPO levels were accessed using 25 µl of the supernatant of the homogenized sample and 25 µl of a solution of 1.6 mM of 3,39-5,59-tetramethylbenzidine (TMB; Sigma—dissolved in dimethyl sulfoxide) and 0.01 mM of $H_2O_2$, dissolved in phosphate buffer (pH 5.4) containing HTAB [Russo, R. C., et al., *Role of the chemokine receptor CXCR2 in bleomycin-induced pulmonary inflammation and fibrosis*. Am J Respir Cell Mol Biol, 2009. 40(4): p. 410-21].

Virus Quantification—Plaque Assay

For virus titrations, lungs collected in sterile conditions were weighted and homogenized in sterile cold PBS. Serial dilutions of samples were incubated in MDCK cells monolayers for 1 hour, covered with agarose for 72 hours as previously described [Garcia, C. C., et al., *Platelet-activating factor receptor plays a role in lung injury and death caused by Influenza A in mice*. PLoS Pathog, 2010. 6(11): p. e1001171]. The number of plaque forming units was expressed per gram of lung.

Histological Analyses

In order to access lung damage followed by IAV and pneumococcus infections, fixed left lobes of the lungs were gradually dehydrated in ethanol and embedded in paraffin. 4 mm sections were cut and stained with H&E for examination under light microscopy. The histopathological score was performed by a pathologist blinded to the experimental groups and evaluated airway, vascular and parenchymal inflammation an also 5 points of general neutrophilic inflammation, in a total of 18 points score [Garcia, C. C., et al., *Platelet-activating factor receptor plays a role in lung injury and death caused by Influenza A in mice*. PLoS Pathog, 2010. 6(11): p. e1001171].

Statistical Analyses

Statistics and graphs were performed using GraphPad Prism 4.0. One-way ANOVA, followed by Newman Keuls post-test was used to compare more than two groups and unpaired t-test was used for comparisons between two groups. The survival curves were analyzed by Long-rank test and the weight loss curves were compared using analyses of area under the curve. Results with $p<0.05$ was considered statistically significant.

Results

Figure 1:
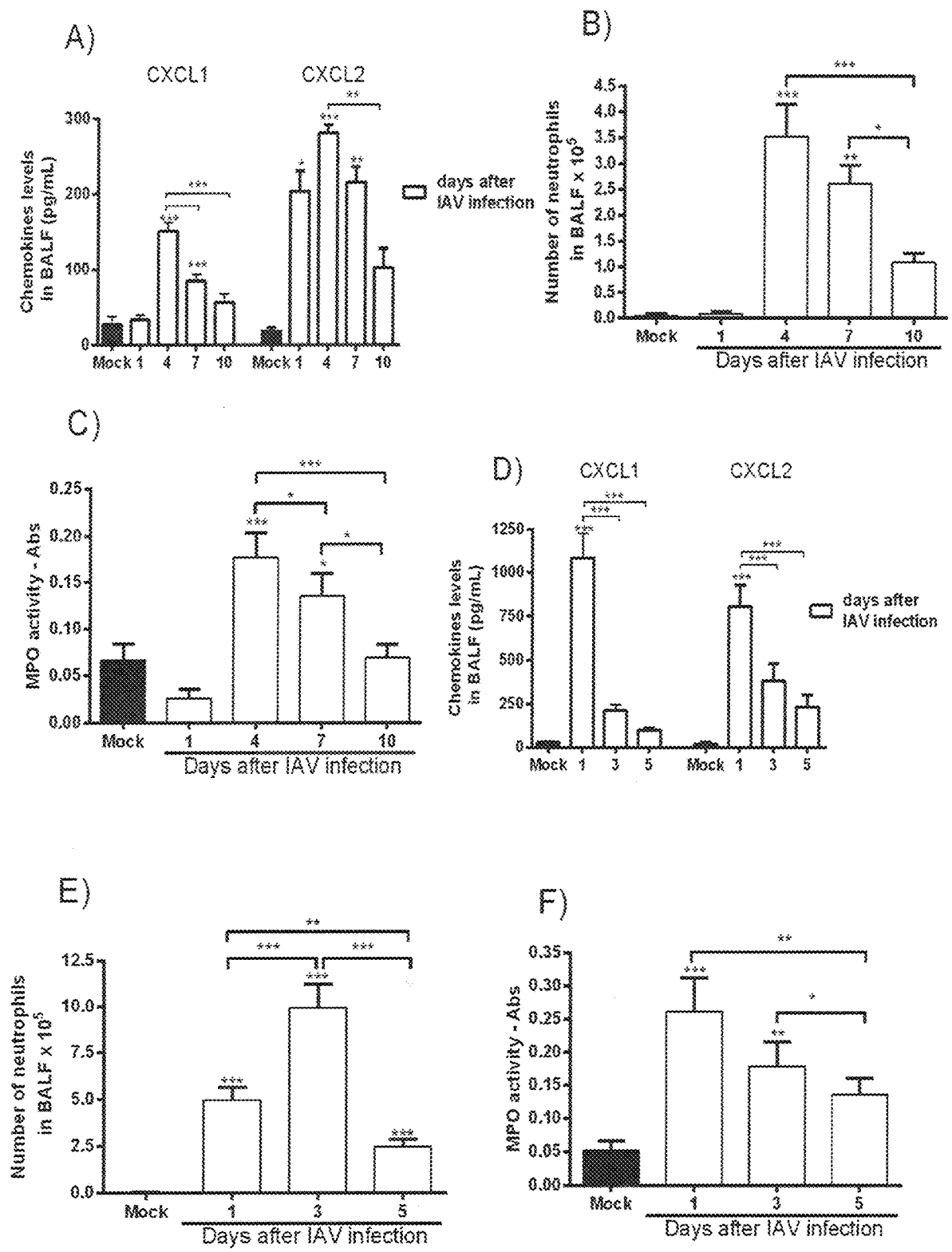
FIG. 1. Kinetics of inflammatory responses triggered by IAV infection. Mice were infected with IAV ($10^4$ and $10^6$ PFU) or instilled with PBS (Mock) and after 1, 3, 4, 5, 7 and 10 days of infection were euthanized. Levels of the chemokines CXCL1 and CXCL2 (A and D), number of neutrophils in the airways (B and E) and lungs (C and F) were evaluated at different times after infection. (n=5-6 mice per group). Results are expressed as the number of cells, levels of cytokines (pg/ml), absorbance or percentage of initial weight and are shown as the mean±SEM. *, $P<0.05$; , $P<0.01$; *, $P<0.001$, when compared with Mock mice or indicated groups.

IAV Infection Increases the Levels of CXCL1 and CXCL2 and to Increased Influx of Neutrophils into the Airways and Lungs of Mice In order to investigate neutrophil infiltration and levels of the chemokines CXCL1 and CXCL2 after lethal and severe IAV infection, mice were infected with $10^4$ (severe inoculum) or $10^6$ PFU (lethal inoculum) of the virus. After 1, 4, 7 and 10 days for the lower inoculum and 1, 3 and 5 days for the higher inoculum, BAL and lungs were collected. Levels of both chemokines in the airways peaked after 4 days of infection with $10^4$ PFU of IAV and decreased thereafter (FIG. 1 A). Infection with the lethal inoculum resulted in faster and higher production of chemokines in the airways of mice (FIG. 1 D). The increased production of CXCL1 and CXCL2 correlated with the massive influx of neutrophils into the airways and lungs of mice and it was inoculum dependent (FIGS. 1 B-C and E-F).

CXCR1/CXCR2 Antagonism Protects Mice During IAV Infection

Figure 2:
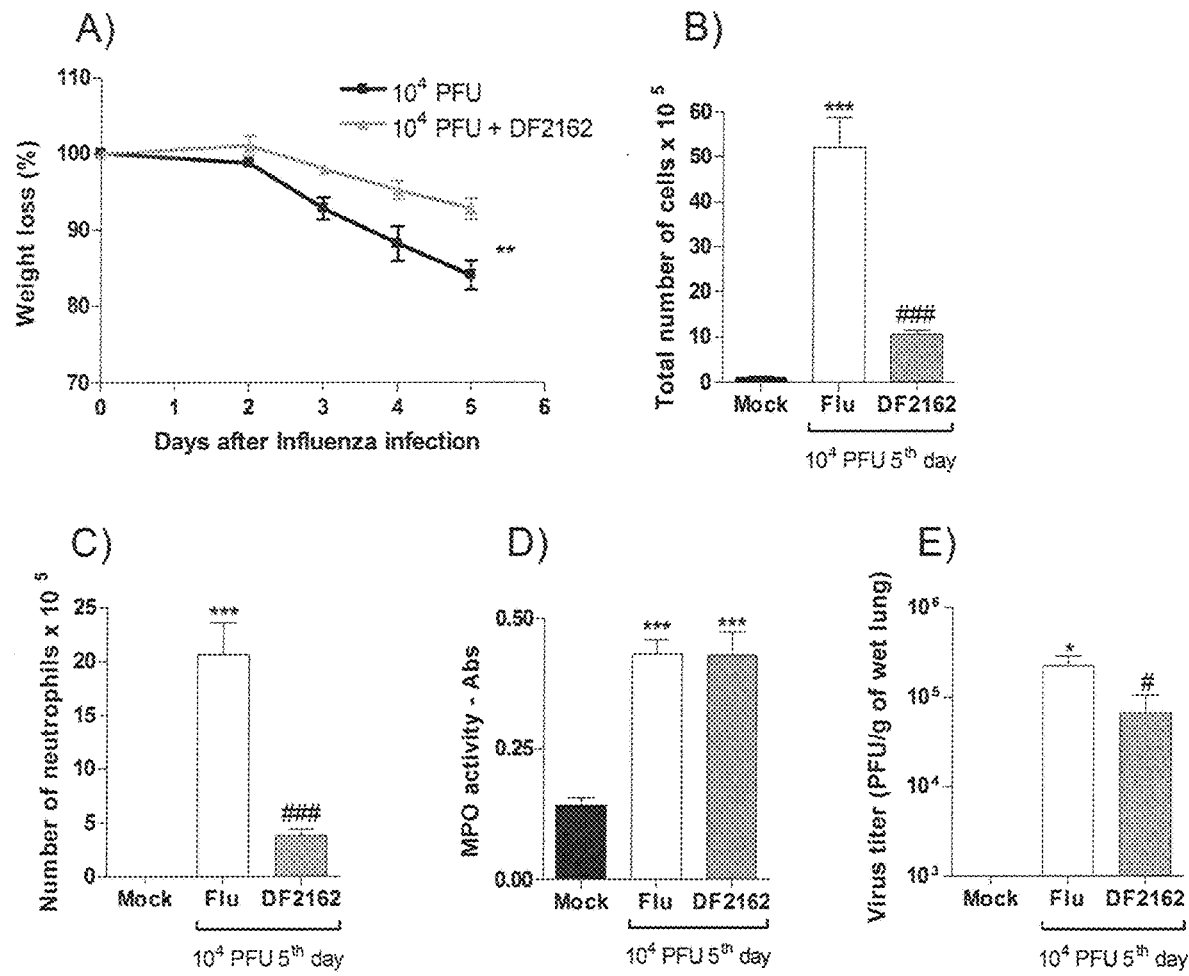
FIG. 2. CXCR1/CXCR2 antagonism decreases the inflammatory responses during IAV infection and protects mice from morbidity. Mice were infected with $10^4$ PFU of IAV and treated with DF2162 (10 mg/kg) twice a day during the first 5 days of infection or with the drug vehicle (CMC 0.1% in PBS). Control animals were instilled intranasally with PBS (Mock). Weight loss (A), number of leukocytes (B) and neutrophils (C) in the airways or lungs (D) and the virus counts in the lungs (E) were evaluated after 5 days of infection. (n=5-6 mice per group). Data are presented as the mean±SEM. * for $P<0,05$;  for $P<0,01$ and * for $P<0.001$, when compared with Mock group and # for $P<0,05$ and ### for $P<0.001$ when compared with vehicle group (Flu).
Figure 3:
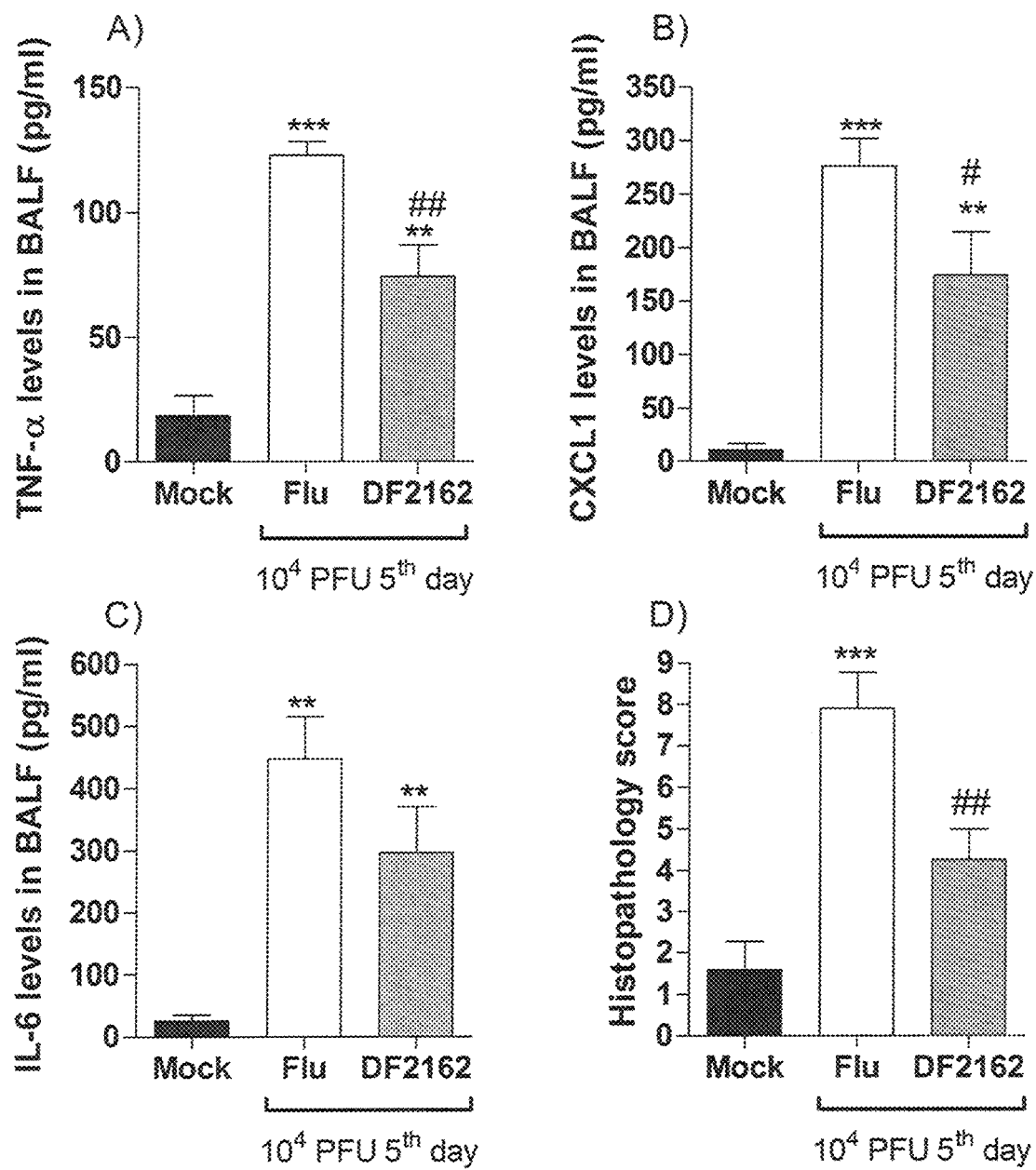
FIG. 3. Levels of pro-inflammatory cytokines and lung damage are reduced after DF2162 treatment. Mice were infected with $10^4$ PFU of IAV and treated with DF2162 (10 mg/kg) twice a day during the first 5 days of infection or with the drug vehicle (CMC 0.1% in PBS). Control animals were instilled intranasally with PBS (Mock). Levels of TNF-α (A), CXCL1 (B) and IL-6 (C) in the airways of mice were measured. Histological analyses were performed and the histopathological score is presented in (D)—maximal of 18 points (airway, vascular, parenchymal inflammation, neutrophilic infiltration and epithelial injury). The results are presented as Mean±SEM (n=5-6 mice per group).  for $P<0.01$ and * for $P<0.001$ when compared to Mock group; # for $P<0.05$ and ## for $P<0.01$ when compared to Vehicle group.

To investigate the role of CXCR1/2 for influenza infection in a therapeutic setting, mice were infected with $10^4$ PFU of IAV and then treated twice a day (from day 0 to day 5 after infection) with DF2162 at a dose that efficiently decreased neutrophil numbers in the lungs of mice [Russo, R. C., et al., *Role of the chemokine receptor CXCR2 in bleomycin-induced pulmonary inflammation and fibrosis*. Am J Respir Cell Mol Biol, 2009. 40(4): p. 410-21]. Treatment with DF2162 decreased morbidity, as seen by the reduction of weight loss (FIG. 2A). Drug treatment also decreased several parameters of the inflammatory response, including number of leukocytes recruited into the airways (FIG. 2B), specially neutrophils (FIG. 2C), and levels of the pro-inflammatory cytokines TNF-α and CXCL1 (FIGS. 3A-B). Treatment with DF2162 did not reduce levels of MPO in the lungs of infected mice (FIG. 2D) or the levels of IL-6 (FIG. 3C). Surprisingly, viral loads in the lungs of treated mice were reduced, as compared with vehicle-treated animals (FIG. 2F). In addition, treatment with DF2162 reduced the lung injury associated with IAV infection (FIG. 3D). Histological analysis showed more preserved areas of lung, with reduced bronchiolar and vascular inflammation in the lungs of treated animals (FIG. 8).

CXCR1/CXCR2 Antagonism Protects Mice During *S. pneumoniae* Infection

Figure 4:
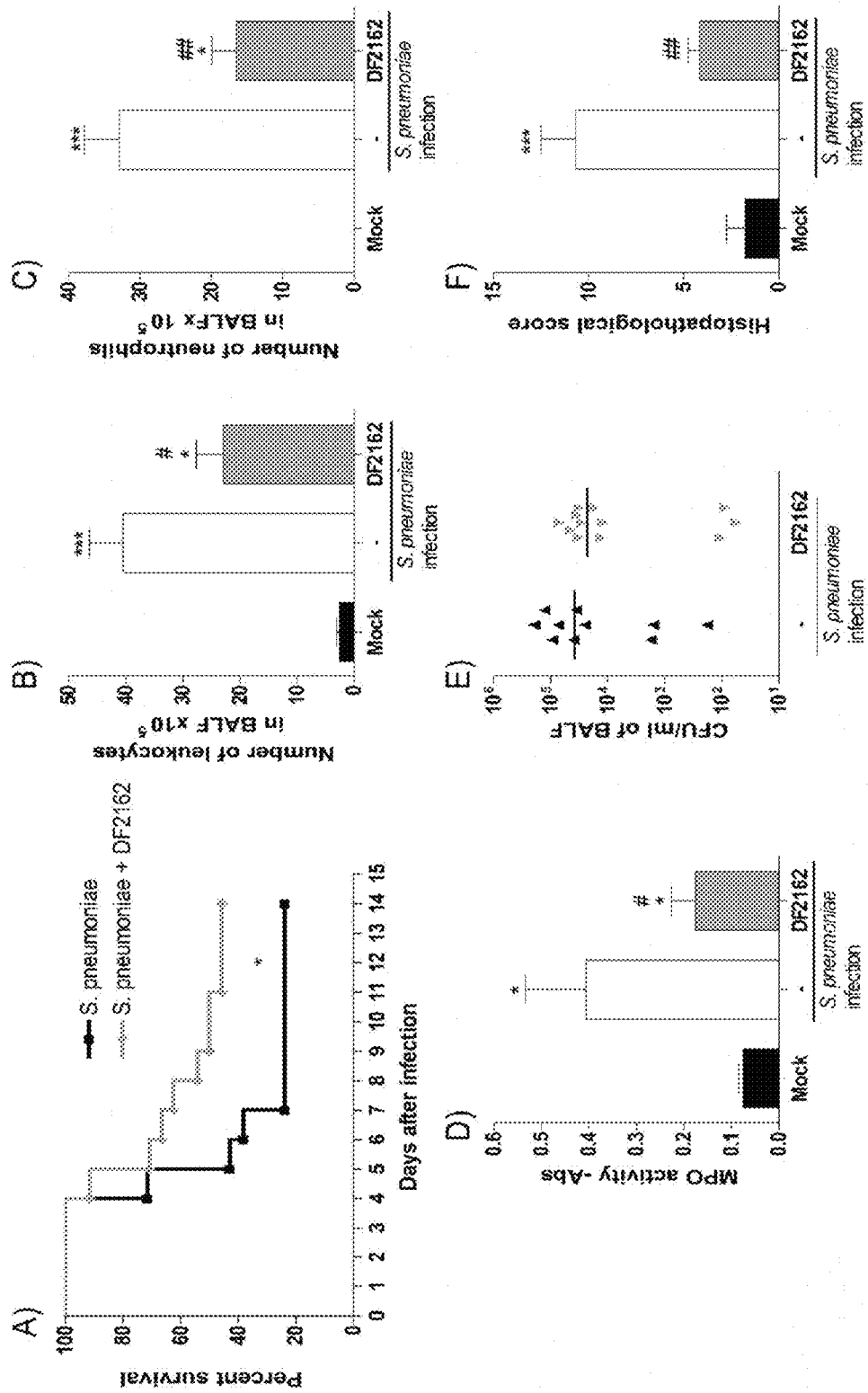
FIG. 4. Effects of CXCR1/CXCR2 antagonism on the course of pneumococcal pneumonia in mice. Mice were infected intranasally (i.n.) with $10^4$ CFU of *S. pneumoniae* or PBS (Mock) and treated with DF2162 (10 mg/kg) twice a day during the first 2 days of infection or with the drug vehicle (CMC 0.1% in PBS). For lethality mice were accompanied daily for 10 days (A). At 48 hours after infection mice were euthanized and the number of total leukocytes (B) and neutrophils in BALF (C) and in the lungs (D) were accessed. Number of bacteria in BALF was also measured (E). Graph F shows the overall pathological score (maximum of 18 points). Results are shown as the median (E) or mean±SEM (all other graphs) of at least six mice in each group.* for $P<0,05$; *** for $P<0.001$, when compared with Mock group and # for $P<0.05$ and ## for $P<0.01$ when compared to vehicle treated group.

Neutrophils are known to be crucial to control the replication and dissemination of bacteria but are also correlated with lung damage and death during pneumococcal pneumonia [Tavares, L. P., et al., *Inhibition of PDE4 During Pneumococcal Pneumonia Reduces Inflammation and Lung Injury in Mice*. Am J Respir Cell Mol Biol, 2015]. Therefore, mice were treated with DF2162 from day 0—6 hours after infection—to day 2 and lethality rates and inflammation parameters were observed. DF2162 treatment in the context of pneumococcal infection protected mice from lethality (FIG. 4A) and this was associated with decreased number of leukocytes (FIG. 4B), especially neutrophils (FIG. 4C) recruited into the airways of infected mice. Surprisingly, despite the reduction in neutrophils in the airways and lungs (FIG. 4D) of infected treated mice, DF2162 did not modify the ability of the host to control the infection as seen by the similar bacterial counts in the airways of mice (FIG. 4E). Furthermore, histological analysis of the lungs of infected mice showed that treatment with DF2162 reduced the lung injury resulting from infection (FIG. 4F and FIG. 9).

CXCR1/CXCR2 Antagonism Protects From a Pneumococcal Infection Following IAV Infection Secondary bacterial pneumonia, mainly caused by *Streptococcus pneumoniae* is a important contributor for the worse prognosis of IAV infected patients, leading to increased mortality and morbidity [Klein, E. Y., et al., *The Frequency of Influenza and Bacterial Co-infection: A Systematic Review and Meta-Analysis*. Influenza Other Respir Viruses, 2016]. During Influenza pandemics, such as the one that occurred in 2009, a significant percentage of the fatal cases were due to secondary pneumococcal infections, despite the use of antibiotics [Palacios, G., et al., *Streptococcus pneumoniae coinfection is correlated with the severity of H1N1 pandemic influenza*. PLoS One, 2009. 4(12): p. e8540; Jain, S., et al., *Hospitalized patients with 2009 H1N1 influenza in the United States*, April-June 2009. N Engl J Med, 2009. 361(20): p. 1935-44; Dominguez-Cherit, G., et al., *Critically Ill patients with 2009 influenza A(H1N1) in Mexico*. JAMA, 2009. 302(17): p. 1880-7]. The exacerbated inflammatory response triggered by the secondary bacterial infection is one of the reasons for this increased mortality.

Figure 5:
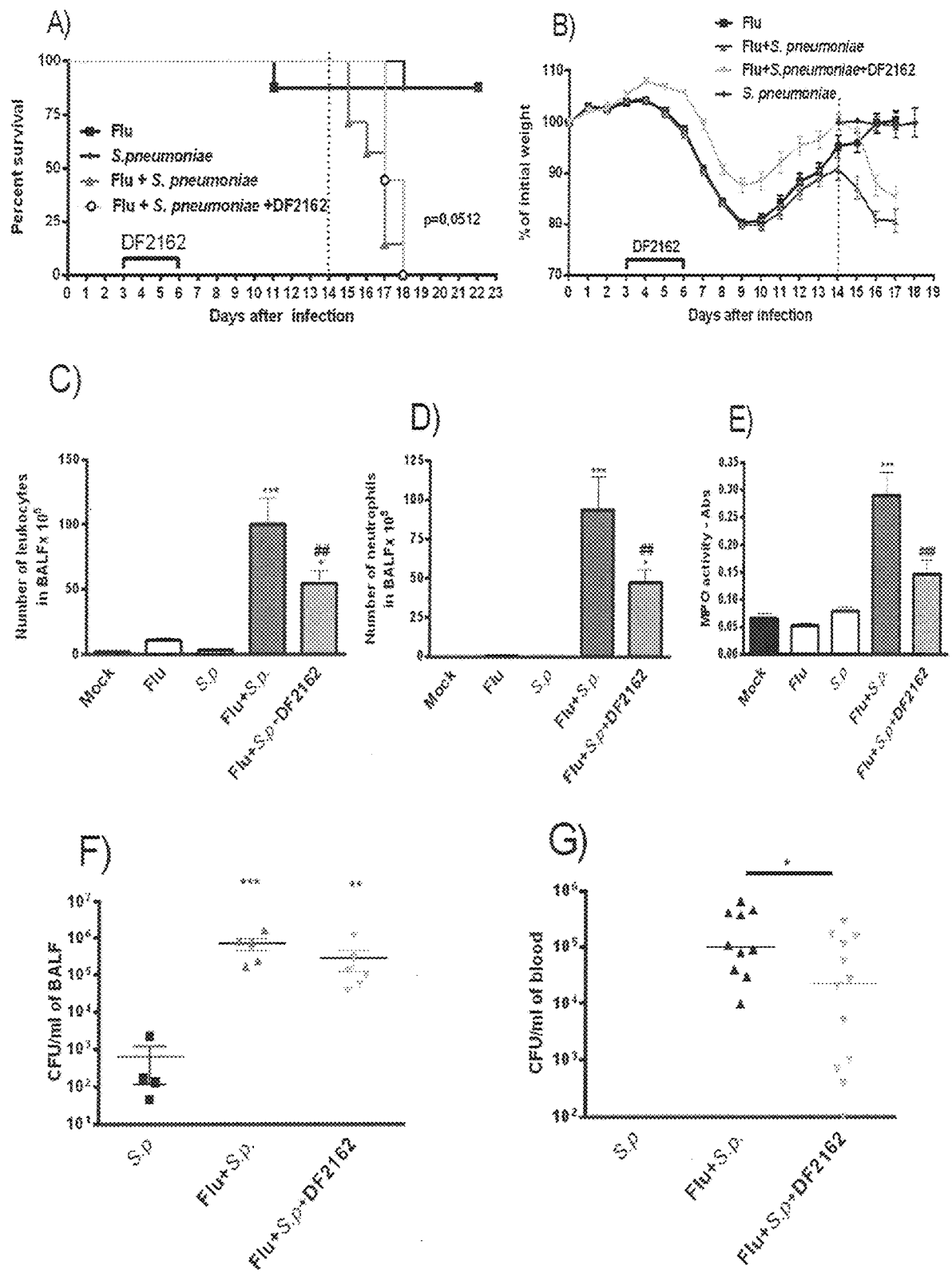
FIG. 5. Weight loss, neutrophils recruitment and bacteria in blood of secondary infected mice are reduced after CXCR1/CXCR2 treatment. Mice were infected with IAV ($5×10^2$ PFU, i.n.) and after 3, 4, 5, and 6 days of infection were treated twice a day with DF2162 (10 mg/kg—oral gavage) or the vehicle of the drug.

In order to investigate the role of CXCR1/2 for secondary bacterial infections, mice were infected with a sublethal inoculum of IAV (500 PFU) and treated with DF2162 or vehicle for the day 3 to 6 of infection. After 14 days of IAV infection, no virus was detected in the lungs of infected mice (data not shown). Mice then received a secondary infection with a sublethal dose of *S. pneumoniae* ($10^3$ CFU, a secondary infection). Control mice received a single infection with either IAV or *S. pneumoniae*. Both single infections resulted in mild disease with low lethality rates and small weight loss (FIG. 5A-B). At 16 days after a single IAV infection or 2 days after a single infection with a low inoculum of pneumococcus, there was no increase in number of neutrophils in the airways or lungs of mice (FIG. 5D-E). In addition, only a small number of bacteria could be found in the airways and no bacteria could be found in blood of mice infected only with *S. pneumoniae* (FIG. 5F-G). In contrast, pneumococcal infection after a IAV infection led to a massive recruitment of neutrophils into the airways and lungs of mice (FIG. 5C-E), overgrowth of bacteria in the airways (FIG. 5F) and their dissemination to the blood (FIG. 5G). This resulted in 100% mortality rates in secondary infected mice (FIG. 5A).

Administration of DF2162 during influenza infection showed that the CXCR1/2 antagonism delayed mortality after secondary infection (FIG. 5A) and reduced the weight loss (FIG. 5B). This was associated with decreased recruitment of neutrophils into the airways (FIG. 5D) and lungs (FIG. 5E) after secondary infection. As reported above, despite the reduction in the number of neutrophils, the present inventors observed that bacteria counts in the airways of mice were not altered (FIG. 5F). Surprisingly, there was a reduction in number of bacteria in the blood of secondary infected mice (FIG. 5G). In addition, treatment with DF2162 prevented the increase of the levels of the pro-inflammatory cytokines IL-6, TNF-α, CXCL-1 and IL-12 that occurred during the secondary infection (FIG. 6A-D). Surprisingly, IL-12 levels remained higher after 16 days of IAV single infection (FIG. 6C). Levels of the anti-inflammatory cytokine IL-10 were also decreased in DF2162 treated mice when compared with the vehicle treated secondary infected mice (FIG. 6E).

Altogether, the decreased influx of neutrophils and cytokine production in mice treated with DF2162 resulted in reduction of the intense lung damage associated with secondary infection (FIG. 7A-B). Single infections with IAV or *S. pneumoniae* sublethal inocula triggered mild airway, vascular and parenchyma inflammation, characterized by discrete leukocyte infiltrate. In contrast, the secondary pneumococcal infection induced massive polimorpho and mononuclear cell migration into the airways with significant loss of parenchyma architecture. The lungs of some mice presented some areas of necrosis and fibrotic tissue. Treatment with DF2162 decreased such histopathological lung damage (FIG. 7C). To confirm these results, levels of protein in the fluid of BAL was used as a marker of plasma leakage, and thus disruption of lung epithelial barrier or tissue injury [Garcia, C. C., et al., *Platelet-activating factor receptor plays a role in lung injury and death caused by Influenza A in mice*. PLoS Pathog, 2010. 6(11): p. e1001171]. The assessment of protein leakage showed that after 16 days of IAV infection, an increase in the levels of protein in BALF is still observed in infected mice. Secondary, but not primary, pneumococcal infection leads to a strikingly protein leakage and, in agreement with the histological results, DF treatment decreased the levels of protein in BALF (FIG. 7C).

The present inventors have also observed that the treatment with DF2162, decreased neutrophil recruitment and the morbidity and mortality associated with both IAV and *S. pneumoniae* infections. The compound according to the invention also prevented lung damage and death associated with subsequent IAV and *S. pneumoniae* infections. Despite the reduction of inflammation, treatment with DF2162 did not reduce the ability to control infection.

Example 2

Effect of CXCR1/2 Pathway in Lung Inflammation Exacerbation Model Combining Viral (Influenza A) Infection and Cigarette Smoke Exposure in Mice Chronic obstructive pulmonary disease (COPD) is a health problem of global importance and rising prevalence accounting for approximately 5% of total deaths worldwide. The disease is characterized by persistent airflow limitation that is usually progressive and associated with an enhanced chronic inflammatory response in the lung airways to noxious particles or gases (Sethi, S. et al. *Am. J. Med.* 125, 1162-1170; 2012). Smoking is the main risk factor and no proper therapy is available.

Increased neutrophil presence in lung tissue is a hallmark in COPD patients often accompanied by an overproduction of inflammatory cytokines such as TNF-α, IL-6 and IL-8 among others. Although neutrophils are undoubtedly major effectors of acute inflammation, several lines of evidence indicate that they also may contribute to chronic inflammatory conditions (Kolaczkowska, E. & Kubes, *Nat. Rev. Immunol.* 13, 159-75; 2013). The major clinical manifestations in COPD include chronic bronchitis, airflow limitation and emphysema, and frequently COPD patients experience exacerbations of these symptoms which dramatically increase morbidity and mortality (Rabe K F et al. *Am. J. Respir. Crit. Care Med.* 532-555; 2007; Jeffery, P. *Chest* Filley Lec, 251S-260S; 2000).

During these exacerbations the number of neutrophils in lung tissue is significantly increased, in parallel with elevation in the levels of matrix metalloproteinases and oxygen reactive species (ROS) enhancing lung tissue remodeling (Oostwoud, L. C. et al. *Nat. Publ. Gr.* 1-16, 2016). Notably, in spite of the importance of inflammation in the pathophysiology of COPD, treatments with glucocorticoids fail to avoid disease progression or prevent its exacerbations. Therefore, new safe and effective treatments for COPD patients are badly needed (Barnes, P. *Nat Rev Drug Discov* 1, 437-446; 2002; Garnock-Jones, K. P. *Drugs* 75, 1645-1656; 2015).

Viral infections are among the principal causes of COPD exacerbations (Mackay, A. J. & Hurst, J. R. *Immunol Allergy Clin North Am* 33, 95-115; 2013). For that reason, the inventors combined influenza infection and cigarette smoke exposure (Cs) in mice in order to model COPD exacerbation. The inventors essentially exposed female C57BL/6 mice to Cs for 12 days and infect them with 1000 pfu of H1N1 influenza virus at day 7 after starting daily Cs exposure (Cs-H1N1). The analyses of lung tissue and bronchoalveolar lavage (BAL) at day 5 post-infection, showed that the combination of viral infection and Cs synergically increased neutrophil infiltration in BAL and MPO activity in lung tissue when compared with viral infection (H1N1) or Cs alone (Cs) (FIG. 10 A-B). It also significantly increased the levels of pro-inflammatory chemokines and cytokines, such as KC and TNF-α as compared with CS or H1N1 infection alone (FIG. 10 C).

Survival assays using a LD50 of influenza virus showed that when combined with Cs, mice mortality rates reaches 80-100% (FIG. 11).

Dexamethasone treatment (1 mg/kg p.o.) in this model decreased mononuclear cell infiltration in BAL but failed to alter the increased neutrophilic infiltration or the increased mortality rate (FIGS. 10 and 11). Since these findings suggest that neutrophils may be the principal contributors of inflammation exacerbation and increased mortality in this model, the inventors performed another survival assay treating Cs-H1N1 mice with DF2156A, a CXCR1/2 antagonist, at 10 mg/Kg p.o. once a day for 7 days starting at the day of infection. DF2156A treatment according to the present invention significantly delayed mice mortality (p<0,0021) which was also slightly reduced. In contrast dexamethasone or Tiotropium treatments showed no significant differences with Cs-H1N1 group of mice.

The invention claimed is:

1. A method of treating secondary pneumococcal infections associated with a preceding influenza infection, in a subject in need thereof, comprising administration of an effective amount of an IL-8 inhibitor, wherein the IL-8 inhibitor is a 2-phenyl-propionic acid derivative of formula (II)

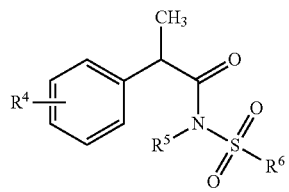

or a pharmaceutically acceptable salt thereof,
wherein:
$R^4$ is linear or branched $C_1$-$C_6$ alkyl, benzoyl, phenoxy, trifluoromethanesulfonyloxy;
$R^5$ is H or linear or branched $C_1$-$C_3$ alkyl; and
$R^6$ is linear or branched $C_1$-$C_6$ alkyl or trifluoromethyl, and wherein the IL-8 inhibitor is administered alone or in combination with one or more pharmaceutically acceptable excipients and/or diluents.

2. The method according to claim 1, wherein the chiral carbon atom of the phenylpropionic group is in the R configuration.

3. The method according to claim 1, wherein the IL-8 inhibitor is R-(−)-2-(4-isobutylphenyl)propionyl methanesulfonamide or a pharmaceutically acceptable salt thereof.

4. The method according to claim 3, wherein the R-(−)-2-(4-isobutylphenyl)propionyl methanesulfonamide is in the form of its lysine in situ salt.

5. The method according to claim 1, wherein the IL-8 inhibitor is R(−)-2-(4-trifluoromethanesulfonyloxy)phenyl]-N-methanesulfonyl propionamide or a pharmaceutically acceptable salt thereof.

6. The method according to claim 5, wherein the R(−)-2-(4-trifluoromethanesulfonyloxy)phenyl]-N-methanesulfonyl propionamide is in the form of its sodium salt.

* * * * *

UNITED STATES PATENT AND TRADEMARK OFFICE
CERTIFICATE OF CORRECTION

| | | |
|---|---|---|
| PATENT NO. | : 12,133,843 B2 | Page 1 of 2 |
| APPLICATION NO. | : 16/616108 | |
| DATED | : November 5, 2024 | |
| INVENTOR(S) | : Laura Brandolini, Marcello Allegretti and Mauro Martins Teixeira | |

It is certified that error appears in the above-identified patent and that said Letters Patent is hereby corrected as shown below:

On the Title Page

Item (56) Under Foreign Patent Documents "2013283022" should read --2013203022--

Item (56) Under Other Publications:

"Kemp DM, et al., "Ladarixin, & dual CKC21/2 inhibitor, attenuates experimental melanomas harboring different molecular defects by affecting malignant cells and tumor microenvironment", Oncotarget, 2017, Vol. 8 (No. 9), pp. 14428-14442." should read --Kemp DM, et al., "Ladarixin, a dual CXCR1/2 inhibitor, attenuates experimental melanomas harboring different molecular defects by affecting malignant cells and tumor microenvironment", Oncotarget, 2017, Vol. 8 (No. 9), pp. 14428-14442.--

"Lopes, et al., "DF275SA, a novel non-competitive allosteric inhibitor of CXCR3./2, reduces inflammatory and post-operative pain", Pharmacological Research, 383 (2016), pp. 69-79." should read --Lopes, et al., "DF2755A, a novel non-competitive allosteric inhibitor of CXCR1/2, reduces inflammatory and post-operative pain", Pharmacological Research, 103 (2016), pp. 69-79.--

"Liderdt, K., et al., "Secondary Bacterial Infections in Patients with Seasonal Influenza A and Pandemic H1N1", BIOMED RES INT., Vol. 2033, Article 376219, 2013, pp 1-6." should read --Liderot, K., et al., "Secondary Bacterial Infections in Patients with Seasonal Influenza A and Pandemic H1N1", BIOMED RES INT., Vol. 2013, Article 376219, 2013, pp 1-6.--

"Morris, D.E., et al., "Secondary Bacterial Infections Associated with Influenza Pandemics", FRONT. MICROBIOL. 2017, Vol. 5, Article 1041, pp 1-17." should read --Morris, D.E., et al., "Secondary Bacterial Infections Associated with Influenza Pandemics", FRONT. MICROBIOL. 2017, Vol. 8, Article 1041, pp 1-17.--

"Barnes, Peter, J., "New treatments for copd", NATURE REVIEWS, Vol. 1, June 2002, pp Signed and Sealed this
Tenth Day of December, 2024

Katherine Kelly Vidal
*Director of the United States Patent and Trademark Office*

CERTIFICATE OF CORRECTION (continued)
U.S. Pat. No. 12,133,843 B2

437-445." should read --Barnes, Peter, J., "New treatments for copd", NATURE REVIEWS, Vol. 1, June 2002, pp 437-446.--